United States Patent [19]
Bolduc et al.

[11] 3,948,259
[45] Apr. 6, 1976

[54] DISPENSING INSTRUMENT

[75] Inventors: Lee R. Bolduc, Minneapolis; Eugene A. Dickhudt, St. Paul, both of Minn.

[73] Assignee: Population Research Incorporated, Minneapolis, Minn.

[22] Filed: Mar. 15, 1974

[21] Appl. No.: 451,530

Related U.S. Application Data

[63] Continuation-in-part of Ser. No. 339,911, March 9, 1973, abandoned, and a continuation-in-part of Ser. No. 438,202, Jan. 31, 1974, Pat. No. 3,875,939.

[52] U.S. Cl. ............... 128/235; 128/349 B; 128/1 R
[51] Int. Cl.² ........................................... A61M 1/00
[58] Field of Search ............ 128/235, 1 R, 232, 230, 128/240, 241, 349, 260, 246, 224, 127–130

[56] References Cited
UNITED STATES PATENTS

| | | | |
|---|---|---|---|
| 3,805,767 | 4/1974 | Erb | 128/1 R |
| 3,817,248 | 6/1974 | Buckles et al. | 128/260 |

OTHER PUBLICATIONS

The Effect of Methyl Cyanoacrylate Tissue Adhesive on the Human Fallopian Tube and Endometrium by Stevenson et al., Journal of Obstetrics and Gynaecology of the British Commonwealth, Nov. 1972, Vol. 79, pp. 1028–1039.

*Primary Examiner*—John D. Yasko
*Attorney, Agent, or Firm*—Lew Schwartz; Wayne A. Sivertson

[57] ABSTRACT

A fluid dispensing instrument and method for placing a material in the uterine cavity and moving the material from the uterine cavity to the canals of the Fallopian tubes of a female. The instrument has an elongated probe carrying an expandable sleeve. A housing connected to the probe has a chamber for a container storing the material. A plunger is operable to move the container onto a needle and force the material through the probe and into the uterine cavity. In one form, an actuator is continuously moved into the housing to initially partially expand the sleeve member to displace part of the uterine cavity. Further movement of the actuator dispenses the material from the probe into the uterine cavity. Continued movement of the actuator fully expands the sleeve member to displace the entire uterine cavity and pump the material into the canals of the Fallopian tubes. After the sleeve member is contracted by releasing the fluid pressure applied thereto, the probe is removed from the uterine cavity.

75 Claims, 38 Drawing Figures

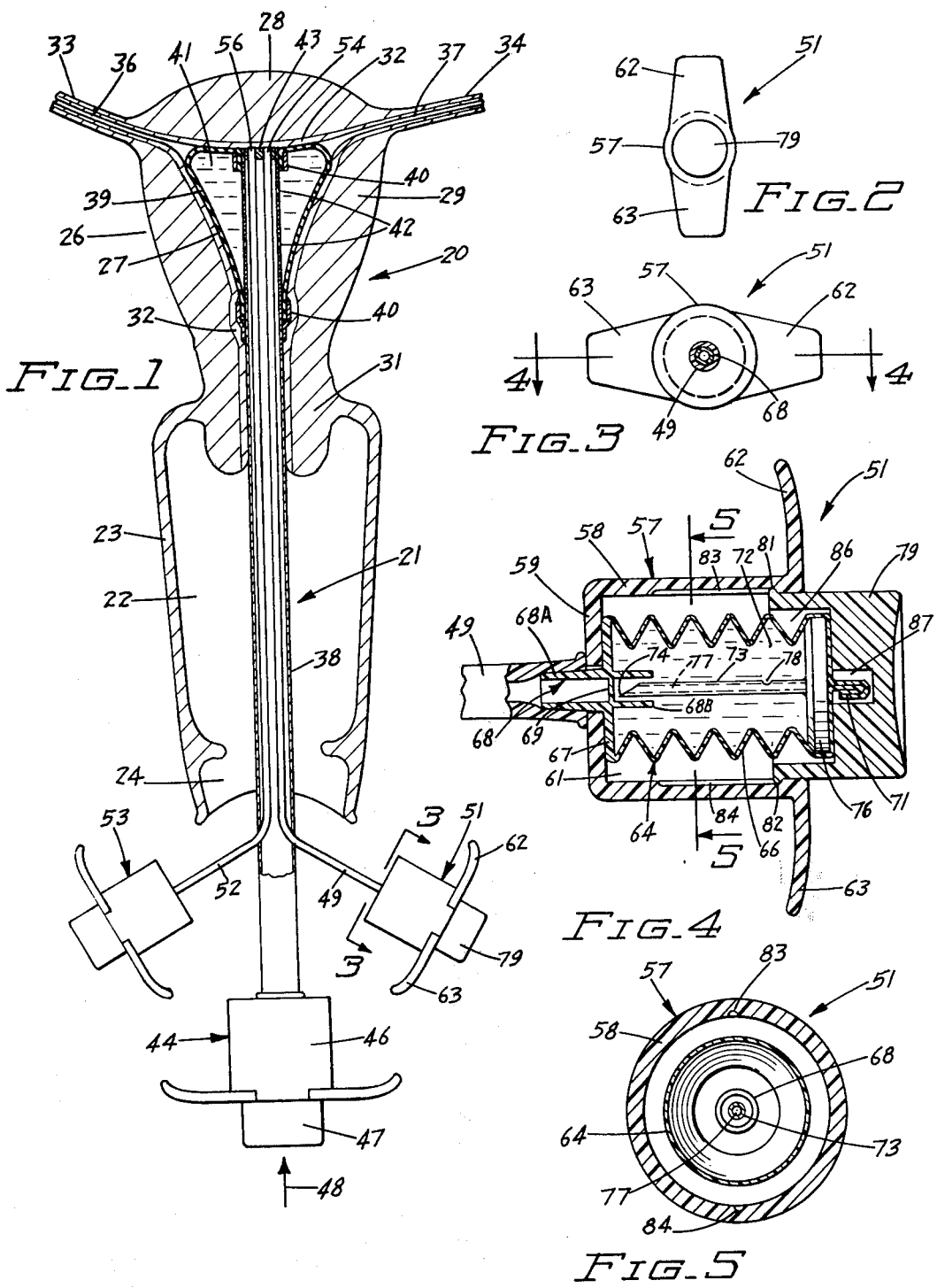

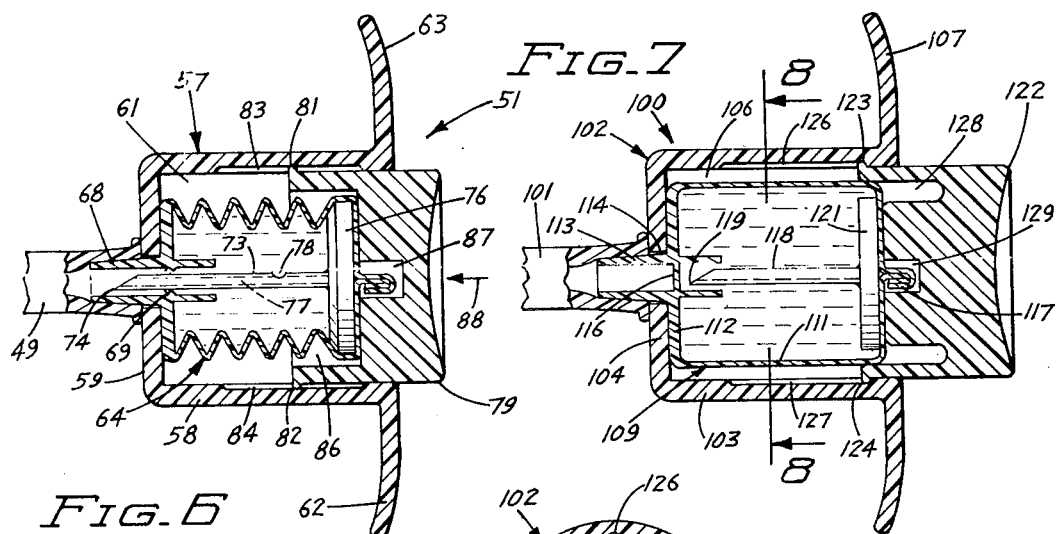
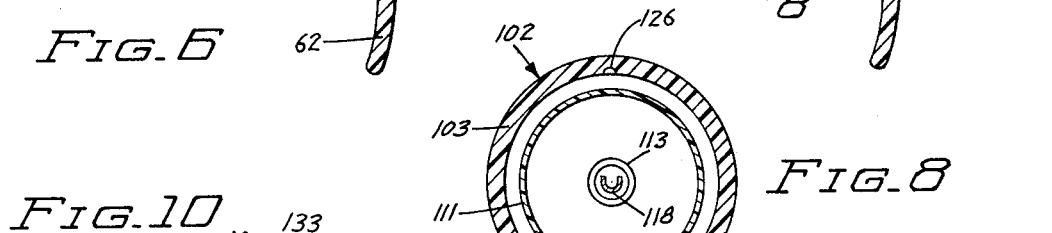

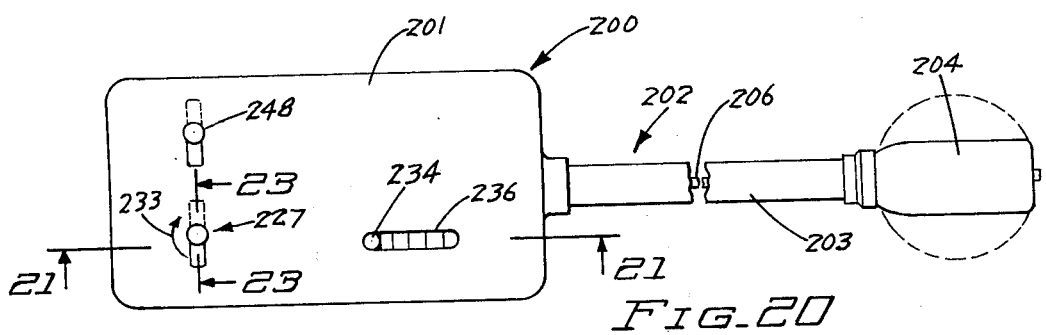
FIG_20
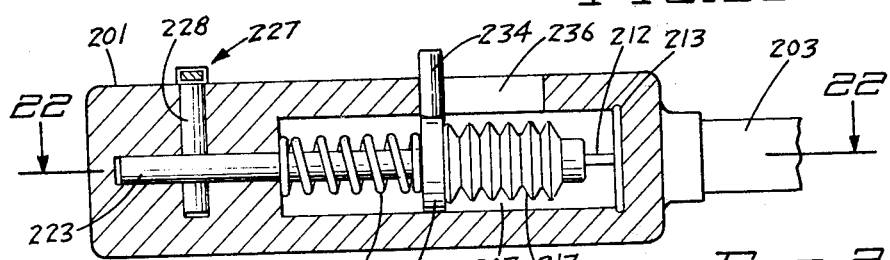
FIG_21
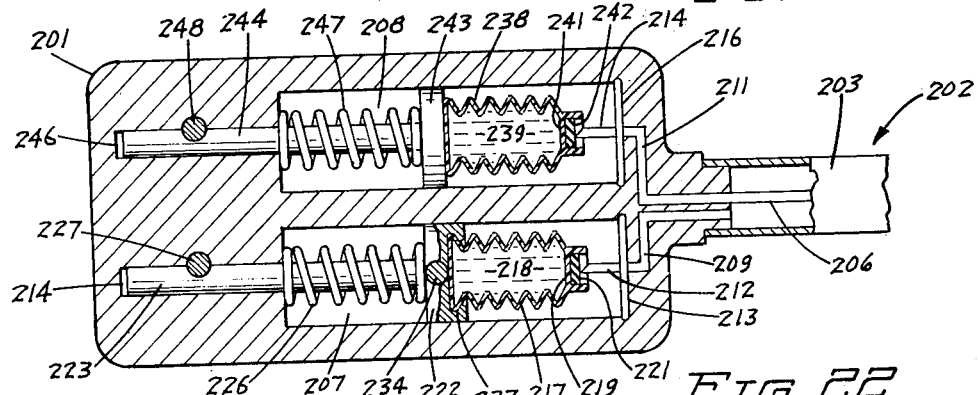
FIG_22
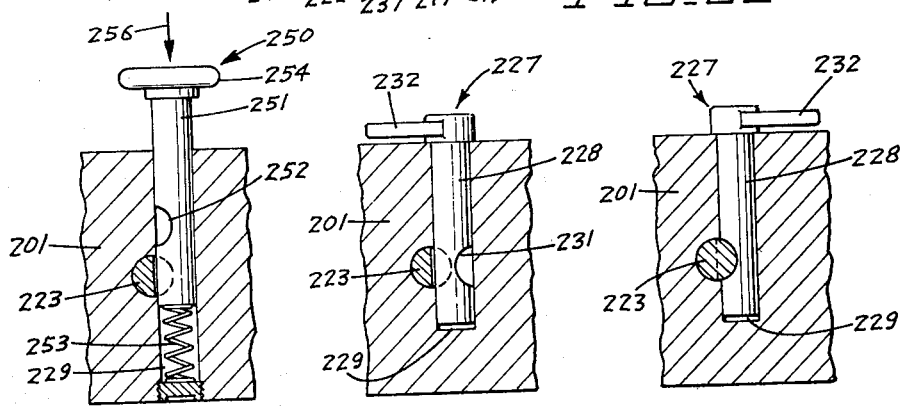
FIG_25  FIG_23  FIG_24

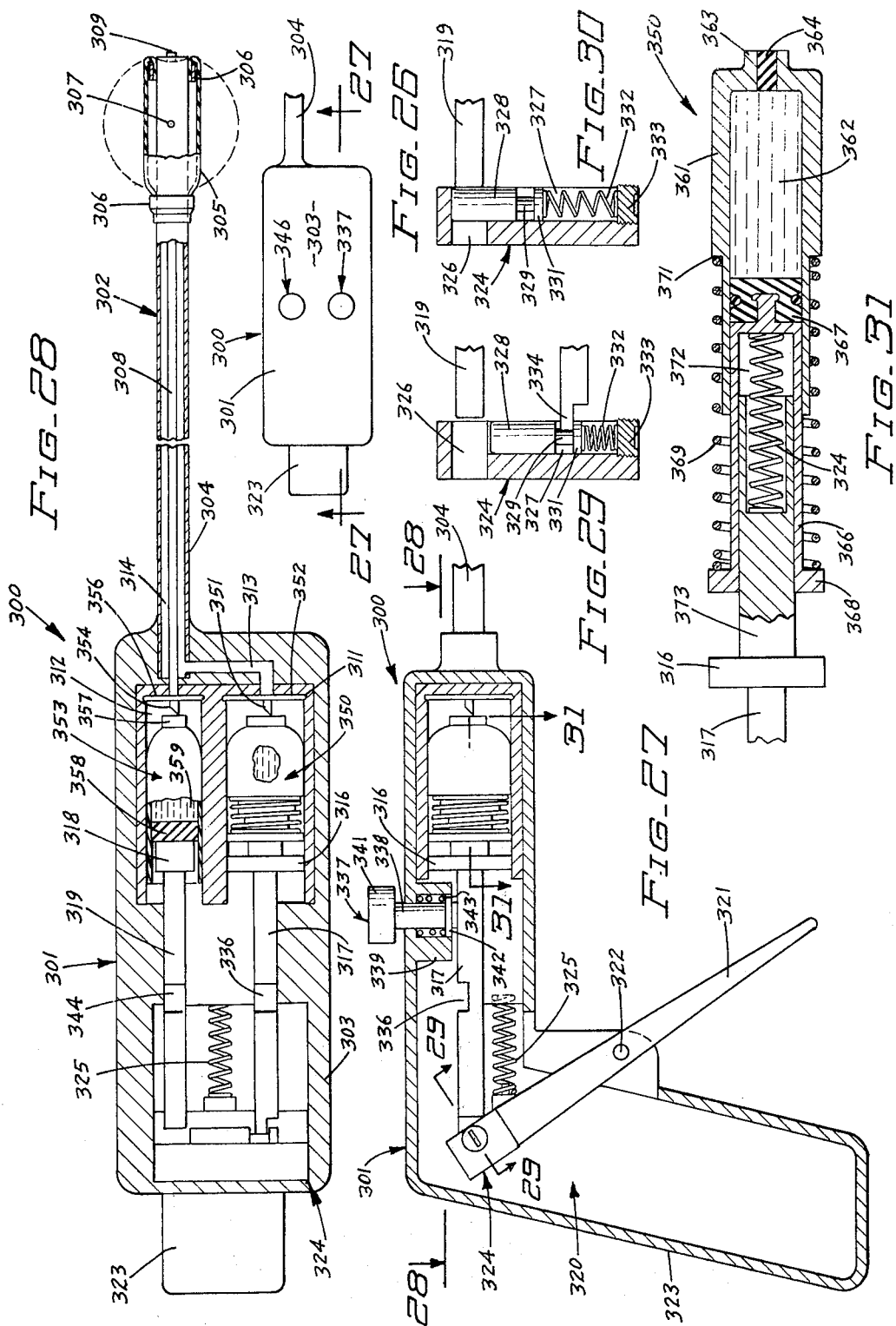

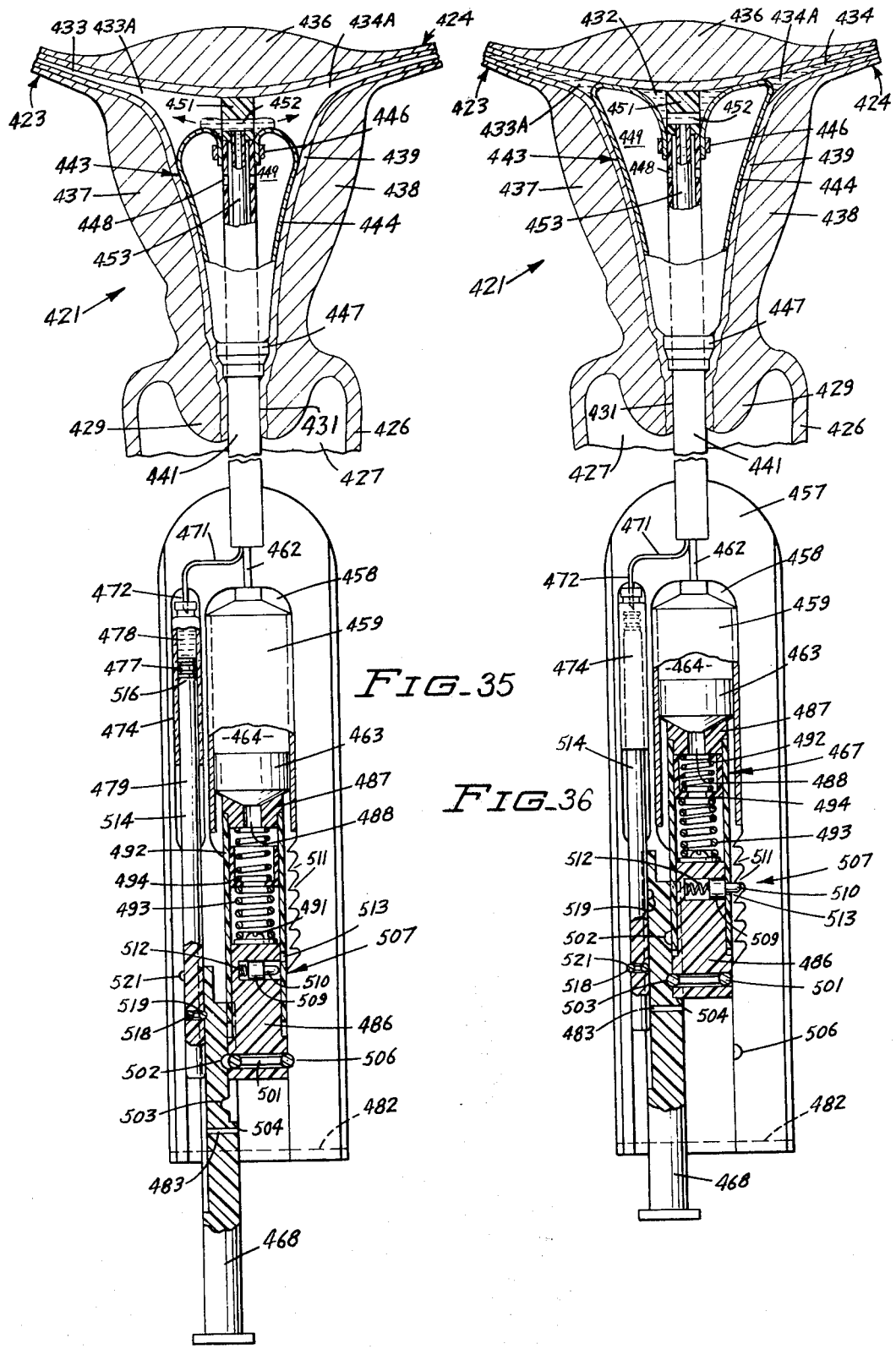

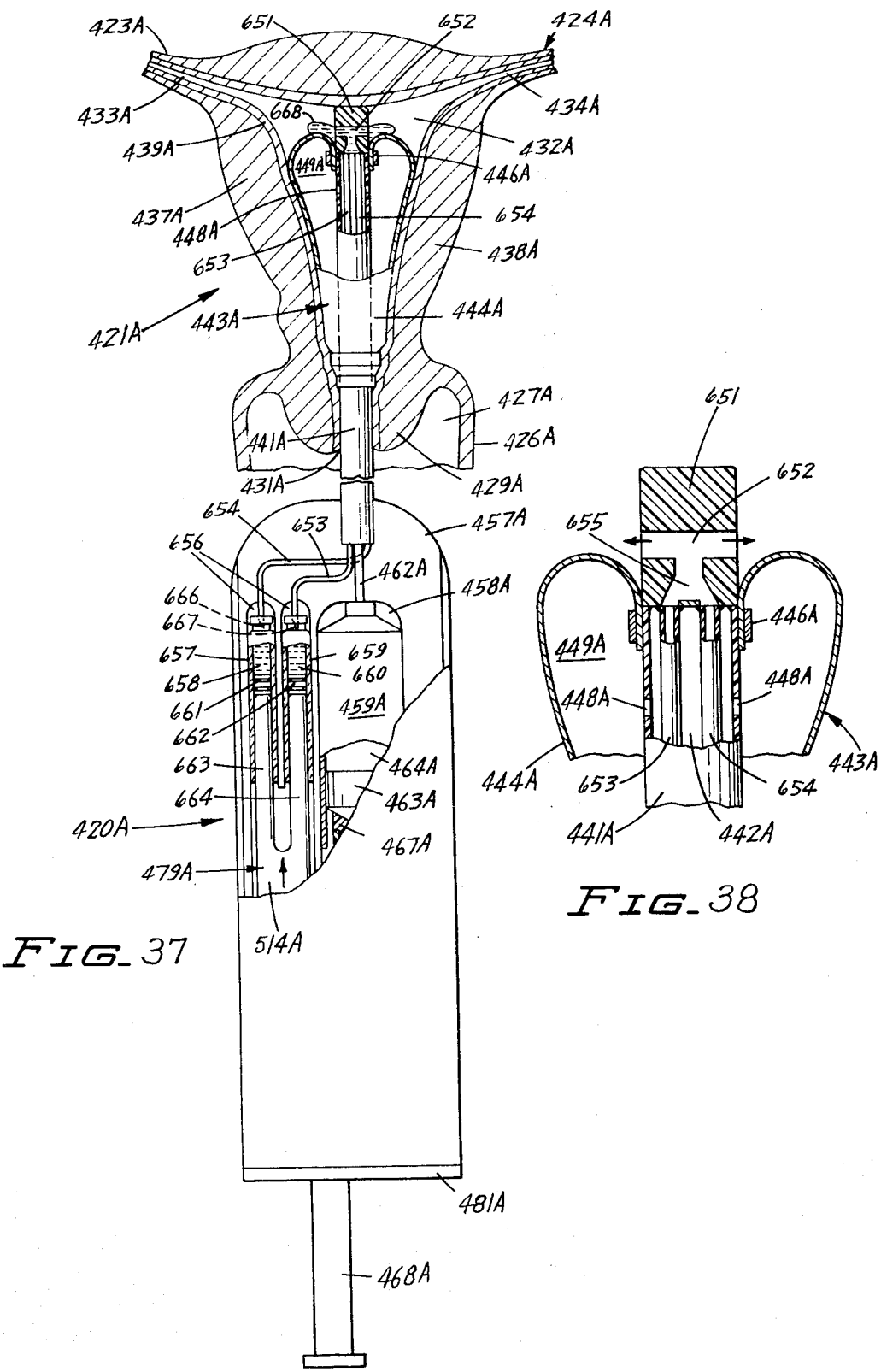

DISPENSING INSTRUMENT

CROSS REFERENCE TO RELATED APPLICATION

This application is a continuation-in-part of U.S. application Ser. No. 339,911 filed Mar. 9, 1973 now abandoned and U.S. application Ser. No. 438,202 filed Jan. 31, 1974 now U.S. Pat. No. 3,875,939

BACKGROUND OF THE INVENTION

Bilateral disection of Fallopian tubes is a common surgical procedure to sterilize a female. This procedure involves severing and tying the Fallopian tubes. Intrauterine devices, as plugs and wires, are used to temporarily sterilize a female. These devices include plugs which are inserted into the canals of the Fallopian tubes to prevent ova from passing from the canals into the uterus. Smith, in 1849, described a method to treat sterility by passing whale bone splints into the canals. These devices do not insure that the ova cannot flow through the canals into the uterus. The devices can be dislodged and lost without the female being aware of it. There is no assurance that the devices are effective. Cimber, in U.S. Pat. No. 3,675,639 and No. 3,680,542, discloses plugs attached to the uterine wall to block the entrance of ova into the uterus from the Fallopian canals and the exit of sperm from the uterine cavity into the Fallopian canal. These plugs are designed to effect temporary sterilization in that they can be removed and do not permanently block the canals of the Fallopian tubes. Plug contraceptive devices are not entirely effective in that it is possible for ova to by-pass the plugs an enter the uterus.

Liquid tissue adhesives have been developed which polymerize when applied to moist living tissue. These adhesives have been used for various surgical procedures. When the tissue adhesives are used the cells adjacent the tissue are damaged and eventually replaced with a fibrous tissue. A liquid tissue adhesive has been injected into the uterine cavity with a catheter to occlude the canals of the Fallopian tubes. Studies have been conducted with silver nitrate, zince chloride and methyl cyanoacrylate to occlude the canals of the Fallopian tubes. These catheters are not designed to accommodate the different sizes, shapes and characteristics of uteri.

Various methods of female sterilization are reviewed by Hulka and Omran in *New Concepts in Contraception*, edited by Potts and Wood and published by University Park Press. The use of tissue adhesives for human sterilization is discussed in *Human Sterilization*, edited by Richart and Prager and published by Charles C. Thomas.

SUMMARY OF THE INVENTION

The invention is directed to an apparatus for dispensing a material, as a drug, into the canals of the Fallopian tubes. The apparatus has a housing having a chamber. Container means storing the material is located in the chamber. Means having a passage for receiving the material from the container means is associated with the housing. Means, as a needle, is operable to puncture a part of the container means whereby material from the container means passes to the passage and the means for receiving the fluid. Actuator means cooperate with the container means and means for piercing the container means whereby material within the container means flows from the container means into the passage for receiving material.

One form of the container means has a collapsible side wall surrounding a chamber for storing one unit of fluid. The needle is located within the chamber whereby the container means material and needle are a compact assembly with the needle protected by the container means. The bottom wall of the container means has a tubular member closed with a diaphragm. The needle pierces the diaphragm when the container means is collapsed whereby the material is dispensed from the container.

One form of the apparatus has a body with a pair of chambers and an elongated first tube adapted to be inserted into the uterine caavity. A second tube within the first tube is connected to one of the chambers. An expandable sleeve attached to the end of the first tube fills the uterine cavity. Fluid, as water or air, under pressure within the sleeve holds the sleeve in firm engagement with the inner wall of the uterus. Containers storing materials are located in the chambers. An actuator mechanism cooperates with the containers to sequentially dispense the materials into the first tube to expand the sleeve and then into the second tube to discharge material, as a drug, tissue adhesive, or the like, into the uterine cavity.

More specifically, the invention is directed to a method and apparatus for introducing a predetermined amount of tissue adhesive into the canals of the Fallopian tubes of a female from the uterine cavity. The apparatus has an elongated probe having a forward end carrying an expandable balloon assembly. A dispensing housing having an actuator is used to expand the balloon assembly and discharge material into the uterine cavity. The dispenser has a first drive assembly operable to initially partially expand the balloon assembly to form a seal and holding structure in the lower portion of the uterine cavity. Continued movement of the actuator discharges the material into the uterine cavity above the partially expanded balloon assembly. Further continued movement of the actuator continues the expansion of the balloon assembly to displace the remaining space in the uterine cavity. The balloon assembly expands and forces the material into both canals of the Fallopian tubes. Substantially all of the material introduced into the uterine cavity is moved by the expanding balloon assembly into the canals of the Fallopian tubes in a short period of time. When a tissue adhesive is placed in the canals, it reacts with the tissue to polymerize the adhesive and thereby occlude the canals. The tissue adhesive is eventually replaced with scar tissue which permanently occludes the canals. The balloon assembly is contracted whereby it can be readily removed from the uterine cavity by withdrawing the actuator from the housing.

The material can be a mixture of materials which set up after they are mixed. Separate materials are moved to the discharge end of the dispenser and mixed at the end. The mixture of materials is directed into the uterine cavity. The expansion of the balloon assembly forces the mixture of material into the canals of the Fallopian tubes.

The invention includes the method of occluding the canals of the Fallopian tubes by inserting an instrument having an expandable sleeve into the uterine cavity through the cervical opening. The expandable sleeve is subjected to fluid under pressure to hold the sleeve in firm uniform engagement with the inner wall of the uterus. A fluid, as a drug, tissue adhesive or the like, is delivered via the instrument to the upper section of the uterine cavity. The fluid flows over the top of the expanded sleeve and into the canals of the Fallopian tubes. Tissue adhesive fluids react with the moisture in the tissue of the Fallopian tubes to set up the adhesive, thereby blocking the canals. Other types of fluids can be injected into the canals to kill the tissue of the canal linings. This tissue is replaced with scar tissue which occludes the canals. The instrument is removed from the uterine cavity after the sleeve is deflated by draining the fluid therefrom.

An object of the invention is to provide an apparatus and method of introducing a predetermined minimum amount of material into both canals of the Fallopian tubes of a female from the uterine cavity. Another object of the invention is to provide a dispensing apparatus and method which has an actuator movable to discharge tissue adhesives into the uterine cavity and move the tissue adhesives from the uterine cavity into the canals of the Fallopian tubes of a female before the adhesives can set up in the uterine cavity. Another object of the invention is to provide an apparatus for introducing in a short period of time a controlled amount of material into the canals of the Fallopian tubes under low pressure with a single and continuous action on the part of the operator. A further object of the invention is to provide an apparatus for introducing material into the canals of the Fallopian tubes which places a minimum amount of force on the walls of the uterus and can accommodate different sizes, shapes and characteristics of uteri. A further object of the invention is to provide an apparatus and method for introducing material into both canals of the Fallopian tubes which is not position sensitive and does not apply substantial pressure to the material, whereby the material is not forced into the blood stream or body cavity. Yet another object of the invention is to provide an apparatus and method of introducing material into both canals of the Fallopian tubes with the balloon assembly subjected to a maximum predetermined pressure to eliminate over-expansion of the uterus. A still further object of the invention is to provide an apparatus for placing material into the canals of the Fallopian tubes which is simple to operate and is used with a minimum of manipulative delay. Another object of the invention is to provide an apparatus and method for mixing separate materials, directing the mixing materials into the uterine cavity and forcing the mixed materials in the uterine cavity into the canals of the Fallopian tubes. Other objects and advantages of the apparatus and method of the invention are set out in the following specification and accompanying drawings.

IN THE DRAWINGS

FIG. 1 is a longitudinal sectional view of the genital system of a female primate with the dispensing instrument extended into the uterine cavity;

FIG. 2 is a top elevational view of the dispensing unit of the instrument;

FIG. 3 is an enlarged sectional view taken along the line 3—3 of FIG. 1;

FIG. 4 is an enlarged sectional view taken along the line 4—4 of FIG. 3;

FIG. 5 is a sectional view taken along the line 5—5 of FIG. 4;

FIG. 6 is a sectional view similar to FIG. 4 showing the dispensing unit actuated to discharge fluid therefrom;

FIG. 7 is a cross sectional view of a modified dispensing unit for the dispenser;

FIG. 8 is a sectional view taken along the line 8—8 of FIG. 7;

FIG. 9 is a sectional view similar to FIG. 7 showing the dispensing unit in the discharge position;

FIG. 10 is a diagrammatic view of a further modification of the dispensing unit in a non-dispensing position;

FIG. 11 is a sectional view similar to FIG. 10 showing the dispensing unit in the discharge position;

FIG. 12 is a longitudinal sectional view of a further modified dispensing unit in the non-dispensing position;

FIG. 13 is a view similar to FIG. 12 showing the dispensing unit in the discharge position;

FIG. 20 is a top plan view of a modified dispensing instrument of the invention;

FIG. 21 is an enlarged sectional view taken along the line 21—21 of FIG. 20;

FIG. 22 is a sectional view taken along the line 22—22 of FIG. 21;

FIG. 23 is an enlarged sectional view taken along the line 23—23 of FIG. 20;

FIG. 24 is a sectional view similar to FIG. 23 showing the lock in the release position;

FIG. 25 is a sectional view similar to FIG. 23 showing a modification of the lock;

FIG. 26 is a top plan view of another modification of the dispensing instrument of the invention;

FIG. 27 is an enlarged sectional view taken along the line 27—27 of FIG. 26;

FIG. 28 is a sectional view taken along the line 28—28 of FIG. 27;

FIG. 29 is an enlarged sectional view taken along the line 29—29 of FIG. 27;

FIG. 30 is a view similar to FIG. 29 showing the movable member in the second position;

FIG. 31 is an enlarged sectional view of the fluid container assembly used in the dispensing instrument;

FIG. 35 is a foreshortened sectional view of the female reproductive system accommodating the dispensing instrument shown in section with the balloon assembly partially inflated in the uterine cavity and drug material in the uterine cavity;

FIG. 36 is a foreshortened sectional view similar to FIG. 35 showing the balloon assembly fully expanded in the uterine cavity;

FIG. 37 is a foreshortened plan view, partly sectioned, similar to FIG. 35, of a modification of the dispensing instrument; and FIG. 38 is an enlarged sectional view of the discharge end of the dispensing instrument of FIG. 37.

DESCRIPTION OF THE PREFERRED EMBODIMENTS

Figure 14:
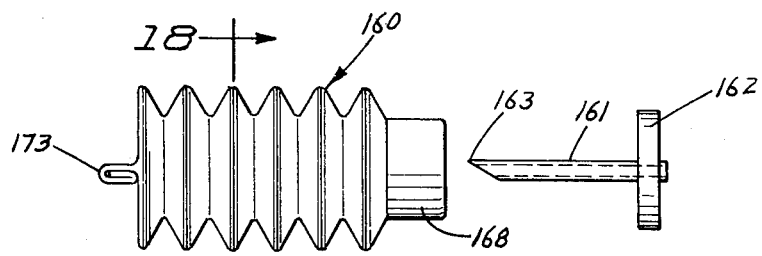
FIG. 14 is a side elevational view of a container spaced from a needle adapted to carry fluid from the container.
Figure 16:
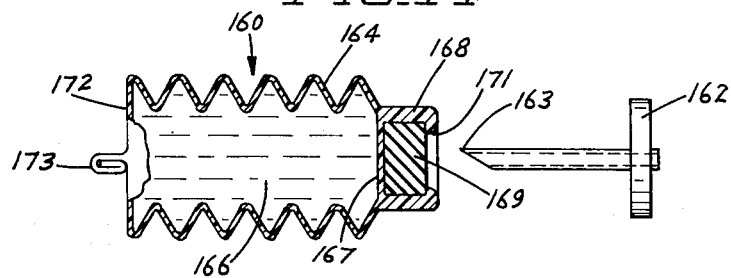
FIG. 16 is a longitudinal sectional view taken along the line 16—16 of FIG. 15.

Referring to the drawing, there is shown in FIG. 1 a diagrammatic female genital system indicated generally at 20. An intrauterine catheter indicated generally at 21 is located in the genital system to direct a fluid, as a drug, tissue adhesive, or other material, into the canals of the Fallopian tubes. The tissue adhesive can be isobutyl 2-cyanoacrylate monomer, silver nitrate or quinacrine materials. The cyanoacrylate monomer is a liquid plastic which sets up or polymerizes in response to moisture and thereby functions to occlude the canals of the Fallopian tubes. The drug materials can be of the type that temporarily block or occlude the canals of the Fallopian tubes. After a period of time the canals will reopen to resume their normal function.

The genital system 20 has an elongated vagina 22 defined by the cylindrical vaginal wall 23. The vagina 22 opens into the vestibule 24. The opposite end of the vagina is attached to the uterus, indicated generally at 26. Uterus 26 is a pear-shaped, thick walled, hollow organ situated between the bladder and rectum. Uterus 26 has a uterine cavity 27 which is flattened and triangular in shape. The size of the uterine cavity varies from female to female. The top or fundus 28 of uterus 26 is joined to the uterus body 29. The lower end of the body contains the cervix 31 which separates the vagina 22 from the uterine cavity 27. The uterine wall is composed of an outer serosal layer, or peritoneum; a firm, thick, intermediate coat of smooth muscle tissue, or myometrium; and an inner mucosal lining, or endometrium 32.

Leading to the upper part of opposite sides of the uterus 26 are Fallopian tubes 33 and 34. The Fallopian tubes are paired, trumpet-shaped, muscular members which extend from the superior angles of the uterine cavity to the ovaries (not shown). The ovaries are solid, slightly irregular shaped bodies situated on either side of the uterus behind and below the Fallopian tubes.

Fallopian tubes 33 and 34 each have a canal or aqueduct 36 and 37 respectively. The Fallopian tubes are musculomembranous structures about 12 cm. in length. They are commonly divided into isthmus, intramural and ampullary sections. The canals 36 and 37 provide passages for the movement of ova from the ovaries into the uterine cavity. The intramural section of the Fallopian tubes traverses the uterine wall in more or less straight fashion. It has an ampulla-like dilation just before it communicates with the uterine cavity 27. The canals 36 and 37 are narrowest at the intramural sections. The walls of the Fallopian tubes consist of three layers; a serosal layer, a muscular layer and a mucosal lining. The muscular layer includes longitudinal muscle fibers which, when contracted, bring the ends of the Fallopian tubes in close contact with the surface of the ovaries. Blood vessels are abundant in the muscular layer where they form with the muscle bundles a kind of erectile tissue which, if engorged, moves the Fallopian tubes to sweep over the surface of the ovaries. This movement of the Fallopian tubes is impaired when the tubes are severed and tied. Occluding the canals 36 and 37 with the drug material according to the invention does not interfere with the erectile action and movement of the Fallopian tubes.

Catheter 21 has an elongated first tube 38 having a length sufficient to extend through the vagina and into the uterine cavity 27. An expandable sleeve member 39, as a balloon or the like, is secured to the upper end of tube 38 with bands 40. The outer end of sleeve member 39 terminates at the outer end of tube 38. Sleeve member 39 is a flexible elastic member made of relaxed rubber material. The rubber material has uniform surface tension and uniform expansion characteristics. Sleeve member 39 is expanded into uniform and firm engagement with the inner wall of the uterus regardless of the size of the uterine cavity. This enables the same catheter construction to be used on all types of primate females. Expanded sleeve member 39 has a generally pear-shaped chamber 41 filled with fluid, as water, air or the like. The tube 38 has a plurality of holes 42 connecting the passage of tube 38 with chamber 41. The upper end of tube 39 is closed with a plug 43.

The end of tube 38, projected from the vestibule 24, is attached to a fluid dispensing unit indicated generally at 44. Tube 38 can be releasably attached to dispensing unit 44 or fixed to dispensing unit 44. The dispensing unit has a body 46 carrying a movable plunger 47. When plunger 47 is moved in the direction of arrow 48, a fluid, preferably water, is forced from the dispensing unit 44 into the expandable sleeve member 39 to form a closure and fill the uterine cavity 27.

Located within the tube 38 are a pair of smaller tubes 49 and 52 for carrying fluids into the uterine cavity 27. Tube 49 has a portion extended outwardly from the tube 38 and attached to a dispensing unit 51. Tube 52 is attached to a dispensing unit 53. Dispensing units 51 and 53 are identical in construction and can be used to dispense the same fluids or different fluids at separate time intervals. One of the dispensing units can dispense a neutralizer fluid into the uterine cavity. The following description is limited to dispensing unit 51.

Referring to FIGS. 2 to 5, dispensing unit 51 has a body or housing 57 comprising a cylindrical side wall 58 and an end wall 59. Housing 57 has a chamber 61 and outwardly directed ears 62 and 63. Ears 62 and 63 extend in diametrically opposite directions from opposite sides of the open end of body 57 and cylindrical side wall 58. A collapsible container or ampulla indicated generally at 64 is located in chamber 61. The container holds a drug or similar material used in the treatment and/or occlusion of the canals of the Fallopian tubes. The container 64 has an accordion cylindrical side wall 66 secured to a transverse generally flat bottom wall 67. The center portion of bottom wall 67 has longitudinal tubular member 68. Member 68 has an outwardly projected portion 68A and an inwardly directed portion 68B. The tubular member 68 is closed with a transverse diaphragm 69. Diaphragm 69 is a relatively thin disc member located in the transverse plane of bottom wall 67. The opposite end of the container 64 is closed with a transverse seal 71.

Container 64 is preferably made of a deformable lead alloy having good moisture and vapor barrier properties. Other deformable material having good moisture and vapor barrier properties can be used to fabricate the container. These properties are important to prevent moisture and vapor sensitive material from polymerizing or setting up during storage periods. The material of the container is also chemically inert to the fluid stored in the container.

Located within the container 64 is a longitudinal needle 73. Needle 73 is a hollow member terminating in an inclined end having a point 74 located adjacent the inside of diaphragm 69. The opposite end of needle 73 is attached to a circular head 76. As shown in FIGS. 4 and 5, needle 73 has a longitudinal passage 77 extended through the pointed end of the needle. The side wall of needle 73 has a hole 78 to provide for the flow of liquid form the container through the needle. Needle 73 can have a plurality of holes or an elongated slot to provide for the flow of fluid through the needle.

The chamber 61 is closed with a plunger or movable member 79. A portion of the movable member fits into the chamber and has outwardly directed ribs 81 and 82 extended into longitudinal grooves 83 and 84 in the inside portions of the cylindrical side wall 58. The ribs 81 and 82 hold the plunger 79 in assembled relation with the body and guide the body linearly into the chamber 61. Plunger 79 has in inwardly open recess 86 for accommodating the outer end of container 64. The bottom central portion of recess 86 has a cavity 87 providing a space for the sealed top 71. Plunger 79 can be removed from the side wall 58, enabling the container 64 to be removed from the chamber and replaced with a new container.

Referring to FIG. 6, the dispensing unit 51 is operated by moving the plunger 79 into the chamber 61. This is accomplished by applying a force on the outer end of plunger 79 in the direction of arrow 88. The first and second fingers are placed under the ears 62 and 63. The thumb is used to apply force to the plunger 79. The needle 73 will be moved through the diaphragm 69. The fluid within container 64 will be placed under pressure and forced through the hole 78 along passage 77 and into the tube 49. The tube 49 carries the fluid up into uterine cavity 27. The fluid is discharged from the end 54 and flows along the inner wall of the fundus into the canals 36 and 37 of the Fallopian tubes. Pressure is applied to plunger 79 until all of the fluid in the container 64 is dispensed therefrom. The sleeve member 39, being in engagement with the inner wall of the fundus, limits the amount of fluid that can collect on the inner wall.

The dispensing unit 51 is a disposable item that contains a single dosage or unit of a drug or fluid. The dispensing unit can be used as part of a syringe to inject drugs into a body. The tube 49 can be replaced with a tubular needle which is placed on the outwardly directed tubular member 68. Tubular member 68 can contain threads to releasably hold the needle. Member 68 can be releasably or permanently attached to an elongated delivery tube.

Referring to FIGS. 7, 8 and 9, there is shown a modification of the dispensing unit, indicated generally at 100, operable to discharge fluid, as a drug, under pressure into a tube or hypodermic needle. Tube 101 can be one of the delivery tubes of catheter 21. Dispensing unit 100 has a body or housing 102 comprising a cylindrical side wall 103 joined to a flat end wall 104. Side wall 103 surrounds a cylindrical chamber 106 having an open end opposite end wall 104. Oppositely directed ears 107 and 108 are secured to the open end of the side wall 103.

Located within chamber 106 is a container or ampulla indicated generally at 109 for storing fluid, as drugs, tissue adhesive, water, air, gas, semi-fluids, and the like. Container 109 is a collapsible structure having a cylindrical side wall 111 and bottom wall 112. Bottom wall 112 is located in flat surface engagement with the inside surface of end wall 104. The center portion of bottom wall 112 has a longitudinal tubular member 113. A portion of tubular member 113 extends through a hole 114 in bottom wall 112. Member 113 has an outwardly projected portion 113A and an inwardly directed portion 113B. The midportion of tubular member 113 has a transverse diaphragm or disc 116 closing the passage through the tubular member 113. The opposite or top end of the container is closed with a folded seal 117. A longitudinal needle 118 is located in the container 109. Needle 118 has a point 119 located in the upper or inner portion of the tubular member 113. The opposite end of needle 118 is attached to a transverse head 121. Head 121 is located adjacent the inside of the top wall of the container 109. As shown in FIG. 8, needle 118 is a generally U-shaped cross section. One side of the needle is open to the fluid in the container. This allows the fluid to flow longitudinally along the container past the point 119 when the point pierces the diaphragm 116. The needle can be a longitudinal tubular member having one or more holes providing access to the passage in the needle, as shown by needle 73 in FIG. 6.

A plunger 122 closes the open end of the housing 102. Plunger 122 has a pair of diametrically opposite ribs or projections 123 and 124. The ribs 123 and 124 are located in longitudinally extended grooves 126 and 127 in the inside of side wall 103 of the housing to guide the longitudinal movement of the plunger into the housing. The inner face of plunger 122 has an annular recess 128 to accommodate portions of the container when the container 122 is moved into the chamber 106. The center portion of plunger 122 has a cavity 129 for accommodating the seal 117 of the container.

In use, referring to FIG. 9, force is applied to plunger 122 in the direction of arrow 121. This moves plunger 122 into the chamber 106. The plunger 122 collapses the container 109 and moves the needle through the diaphragm 116. As soon as the point 119 of the needle penetrates the diaphragm 116, the fluid within container 109 can flow through the needle 118 into the tube or receiver 101. Fluid will continue to flow through the needle 118 as long as force is applied to the plunger 122. Plunger 122 can be moved into chamber 106 until the head abuts against the inner portion of tubular member 113.

Referring to FIGS. 10 and 11, there is shown a modification of the needle and container arrangement. The bottom portion of container 132 has a generally flat end wall 133. The midportion of the end wall has a longitudinal tubular member 134. The tubular member 134 has an outwardly directed outer portion 134A and an inwardly projected inner portion 134B. The midportion of the tubular member 134, in general alignment with the end wall 133, has a diaphragm or disc 136. A needle indicated generally at 137 is longitudinally aligned with the passage in the tubular member 134. Needle 137 has a cone-shaped head 138 terminating in a point. Head 138 is connected to an elongated shank 139. As shown in FIG. 11, when needle 137 is moved in the direction of arrow 141, head 138 punctures the diaphragm 136. The hole in the diaphragm 136 is larger than the shank 139, allowing the fluid in the container to flow past the diaphragm 136 into the discharge portion of the tubular member 134. The outer portion 134C of the tubular member has threads 142 adapted to receive a female threaded member, as a nut or sleeve, or a fluid receiving apparatus. Other types of connections can be used to couple the tubular member 124 to the fluid receiving apparatus.

Referring to FIGS. 12 and 13, there is shown a fluid dispensing container or ampulla indicated generally at 143. The container has a cylindrical side wall 144 surrounding a chamber 145 for storing fluid, as drugs, tissue adhesive, water and the like. Wall 144 is made of non-collapsible material. A generally flat transverse end wall 146 is integral with one end of side wall 144. The center portion of end wall 146 has an elongated longitudinal tubular member 147. Tubular member 147 has an outer portion 147A extended outwardly from end wall 146 and an inner portion 147B projected into chamber 145. The midportion of tubular member 147 is closed with a diaphragm 148. Diaphragm 148 is located in transverse alignment with the end wall 146 and is of a material that can be pierced with a needle.

An elongated longitudinal needle 149 is located within chamber 145. Needle 149 has a forward end located within the passage of inner portion 147B and terminates in a point 151. The opposite end of needle 149 is attached to a transverse head 152. Head 152 has an annular outer peripheral surface which forms a seal 153 with the adjacent inner wall of side wall 144. The outer peripheral surface of the head 152 is in sealing frictional fit with the inner surface of the side wall 144. The outer peripheral surface of the head 152 is in sealing frictional fit with the inner surface of side wall 144 so as to prevent moisture, air or other substances from entering chamber 145. Needle 149 has a generally U-shaped cross section as shown by needle 118 in FIG. 8. Alternatively, needle 149 can be a tubular member having one or more side holes to provide a passage for the movement of fluid in chamber 146 out the end of needle 149. The needle can also have the shape of needle 137, as shown in FIGS. 10 and 11. Other shapes and structures can be used to permit the flow of fluid along the needle through the diaphragm once the diaphragm has been pierced by the point of the needle.

In use, head 152 is moved into chamber 145 in the direction of arrow 154 shown in FIG. 13. The point 151 of the needle will penetrate and pierce the diaphragm 148. The fluid in chamber 145 is forced along the needle through the pierced diaphragm and discharged via the outer portion 147A of the tubular member.

Figure 19:
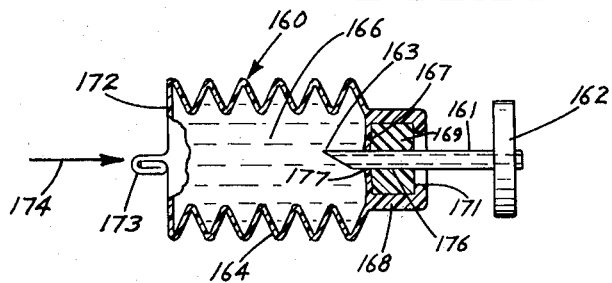
FIG. 19 is a sectional view similar to FIG. 16 showing the container in assembled relation with the needle.

Referring to FIGS. 14 and 19, there is shown a container or ampulla indicated generally at 160 for storing a fluid, as a drug, liquid tissue adhesive, semi-liquid material or a gas. Container 160 is located in longitudinal alignment with a tubular needle 161. Needle 161 is secured to a generally transverse base 162 and has a point or sharp edge 163 at its forward end. Base 162 is mounted in a housing (not shown) to fix the position of the needle 161.

Container 160 is a one-piece body having a continuous side wall 164. Side wall 164 has an accordian shape and is of a cylindrical configuration and surrounds a chamber 166 for storing the fluid. The forward end 167 is closed with a diaphragm or cylindrical disc member comprising an end wall 167. An outwardly directed longitudinal sleeve 168 is attached to the outer peripheral edge of the end wall 167 forming an extension of the container. A disc or pad 169 of resilient material, as sponge rubber, plastic foam or the like, is located within sleeve 168 and covers the end wall 167. Sleeve 168 has a rolled outer edge or bead 171 holding the pad within the sleeve 168.

Figures 15, 17, 18:
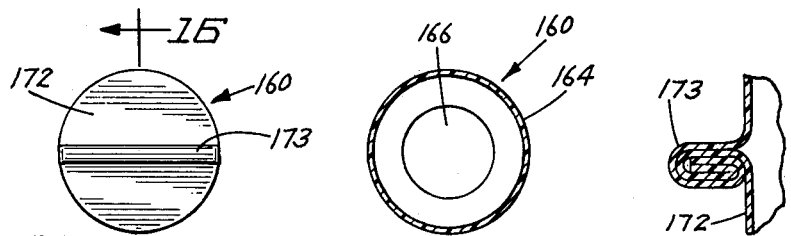
FIG. 15 is an end elevational view of the sealed end of the container of FIG. 14.
FIG. 17 is an enlarged sectional view of the sealed end of the container.
FIG. 18 is a sectional view taken along the line 18—18 of FIG. 14.

The rear end of the container is closed with an end wall 172. End wall 172 has a transverse seam 173 closed to moisture and vapor to seal the container. As shown in FIG. 17, the seam 173 has lapped and inturned edges that are sealed together. The container is made of a material having moisture and vapor impervious properties. Preferably the material is deformable lead alloy which is chemically inert to the fluid stored in the container. Other deformable materials having good moisture and vapor barrier properties can be used to form the container. These properties are essential to prevent moisture and vapor sensitive materials from setting up or polymerizing during lengthy storage periods. For example, the cyanoacrylate monomer is extremely sensitive to moisture and vapor. It must be stored in a sealed container which does not allow ingress of moisture and vapor. The monomer will set up in a short period of time when exposed to moisture, including the moisture of tissues.

In use, force is applied to the end wall 172 in the direction of arrow 174. This force moves the container 160 into operative engagement with needle 161. The force will also collapse the side wall 164 and apply sufficient force to the container whereby the needle 161 will cut through or pierce both the pad 169 and end wall 167. Pad 169, being made of resilient elastic material, will be formed with a hole 176 in tight sealing engagement with the outer peripheral surface of needle 161. Needle 161 will also make a hole 177 in the end wall 167. Needle 161, being a hollow tubular member, provides a passage for the flow of fluid from chamber 166 into a fluid receiver such as the tube of the dispensing catheter.

Referring to FIG. 20, there is shown a catheter dispenser having a dispensing unit indicated generally at 200 attached to an elongated balloon catheter 202. The dispensing unit has a body or housing 201 attached to an elongated linear tube 203 of the catheter. Tube 203 can be an integral extension of the body or releasably connected to the body 201. The outer end of the catheter has an expandable sleeve member or balloon 204 adapted to confine fluid, as water or gas, to enlarge the expandable sleeve member 204. As shown in FIG. 22, a second smaller tube 206 is located within the tube 203. Tube 206 extends the entire length of the tube 203 and has an outlet opening 205 at the outer end whereby fluid can be discharged from the catheter. The outer end of tube 203 can be recessed to insure the flow of fluid from outlet opening 205.

The body 201, as shown in FIG. 22, has a pair of longitudinally extended chambers 207 and 208. Chambers 207 and 208 are located side-by-side in a generally horizontal plane. The chambers can be located in a generally vertical plane. A passage 209 connects the chamber 207 with the passageway of tube 203. A similar passage 211 connects the chamber 208 with the passage in tube 206. A short tubular needle 212 extends longitudinally into passage 207. Needle 212 is attached to a transverse base 213 positioned at the end of chamber 207 having the passage 209. The outer peripheral edge of base 213 is located in a groove in the housing to fix the position of the base and needle relative to the passage 207. The needle 212 has a passage in alignment with passage 209 so that fluid flows through the needle into the passage 209.

A second tubular needle 214 is located longitudinally in passage 208. Needle 214 is attached to a base 216 located at the end of chamber 208 adjacent the passage 211. The outer peripheral edge of base 216 is located in grooves in the housing 201 to fix the position of the base and needle relative to passage 208. The passage of needle 214 is aligned with the passage 211 so that the fluid can flow through the needle and into passage 211.

A container or ampulla 217 having a chamber 218 for fluid, as drugs, water or other material, is located in chamber 207. Container 217 has an end or diaphragm 219 facing the needle 212. A pad 221 of resilient cushioning material is located between diaphragm 219 and the pointed end of needle 212. A plunger 222 is attached to the opposite end of container 217. A suitable dovetail or tongue and groove 237 can be used to connect the container to the plunger. Other types of connections can be used to attach the container to the plunger. A longitudinal rod 223 is connected to plunger 222 and extended into a bore 224 in the housing 201. A coil spring 226 is positioned around rod 223 and engages the housing 201 and the plunger 222 to bias the plunger toward the needle 212.

A releasable lock 227 engages the rod 222 to hold the plunger 221 in a cocked position whereby the diaphragm 219 is held from the needle 212. Referring to FIGS. 23 and 24, releasable lock 227 comprises a cylindrical member or body 228 extended downwardly into a hole 229 in housing 201 through a cutout or groove 230 in rod 223. The body 228 has a semicircular cutout 231 in alignment with rod 223. The upper or exposed end of the body 228 has a handle 232. The handle 232 is movable in the direction of arrow 233 shown in FIG. 20 to move the cutout 231 in registration with rod 223. When the cutout 231 is in registration with rod 223, as shown in FIG. 18, the rod is free to move. The spring 226 will bias plunger 222 toward the needle 212. This moves the container 217 and the diaphragm 219 into the needle 212. The pointed end of the needle will pass through the pad 221 and puncture diaphragm 218. The needle 212 will form a seal with the diaphragm 219 whereby the fluid in chamber 218 will flow through the needle, passage 209 and into the passage of catheter tube 203. The biasing force of the spring 226 will force substantially all of the fluid in chamber 218 through needle 212.

An upwardly directed finger 234, shown in FIG. 21, is attached to plunger 222. The finger 234 extends through a longitudinal slot 236 in the housing 201. The upper end of finger 234 is enlarged so that it can be gripped. Plunger 222 and container 217 have cooperating connections such as a dovetail connection 237, shown in FIG. 22. When force is applied to finger 234, the plunger 222 can be moved to a reverse direction, expanding the container 217. This withdraws the fluid from the catheter, decreasing the size of the expandable member 204. The plunger 222 can be moved until lock 227 can be moved to fix the position of the plunger 222 in the housing. Other types of retraction structure can be used to withdraw and expand the container 217 to relieve the fluid from the expandable member 204.

A container or ampulla 238 is located in chamber 208 adjacent the needle 214. Container 238 has a chamber 239 for storing drugs, tissue adhesive and other materials. Container 238 has an end or diaphragm 241 spaced from the pointed end of needle 214 with a resilient pad 242. Some drugs that are moisture and vapor sensitive require a container made of material having good moisture and vapor barrier properties. Preferably a deformable lead alloy is used to make this type of container. These properties are important to prevent moisture and vapor sensitive materials from polymerizing or setting up during storage periods. The material of the container is also chemically inert to the fluid stored in the container. Located adjacent the opposite end of container 238 is a plunger 243. A longitudinal rod 244 attached to plunger 243 extends into a bore 246 in housing 201. A spring 247 located in chamber 208 engages the housing 201 and plunger 243 to bias the plunger toward the needle 214. The rod 244 is held with a releasable lock 248. Lock 248 is identical to lock 227. It is operated by moving the handle of the lock to the dotted line position, as shown in FIG. 14. This releases the rod 214 whereby the spring 247 will bias the plunger in a forward direction, moving the diaphragm 241 toward the needle 214. The pointed end of needle 214 will pierce diaphragm 241, thereby providing a fluid connection between the chamber and the passage 211 leading to the tube 206. The diaphragm will be located in sealing realtion with respect to the needle whereby the fluid in chamber 239 of container 238 will be forced by the biasing action of the spring 247 through the needle 214, the passage 211 and the passage of the tube 206.

Body 201 has doors or closure members closing openings into the chamber 207 and 208 whereby the containers 217 and 238 can be removed and replaced. Other types of containers as herein disclosed can be inserted into the chambers.

Referring to FIG. 25, there is shown a modification of the releasable lock, indicated generally at 250. Lock 250 has a body or rod 251 having a cylindrical cutout 252. The rod 223 attached to the plunger has a similar cutout. A spring 253 located in the base of bore 224 biases the body 251 in an upward direction. The upper end of body 252 is attached to a head 254.

In use, body 251 has a portion located in the groove or recess in the side of the rod 223 to hold the rod in the cocked position, as shown in FIG. 22. The rod 223 is released by pushing head 254 in a downward direction, as indicated by arrow 256, until the cutout 252 is aligned with rod 223. This releases the holding action on rod 223 whereby the spring 226 can move the rod in a forward direction, forcing the diaphragm 219 into engagement with the needle 212.

Referring to FIGS. 26, 27, 28 and 29, there is shown a further modification of a dispenser catheter of the invention indicated generally at 300 for discharging fluid, as drugs, tissue adhesives, and the like, into the uterine cavity. The dispenser catheter 300 has a dispensing unit 301 and an elongated tubular catheter 302. Dispensing unit 301 has a body 303 attached to elongated tube 304 of the catheter. Tube 304 can be releasably connected or permanently fixed to body 303. Mounted on the end of tube 304 is an expandable sleeve member or balloon 305. Bands 306 clamp the ends of sleeve member 305 to tube 304. Sleeve member 305 is an elastic sheet member, of relaxed rubber, plastic or like materials. When the sleeve member 305 is expanded in the uterine cavity, it applies uniform outward pressure on the uterine wall. The expanded sleeve member 305 prevents the drugs injected into the uterine cavity from contacting substantial portions of the uterine wall and flowing out of the uterine cavity. Holes 307 in the end of tube 304 provide the passageway for the fluid, as water, from within the tube 304 into the area surrounded by the sleeve member 305 to expand sleeve member 305. An elongated small tube 308 is located within tube 304. Tube 308 has a discharge end 309 at the outer end of tube 304.

Body 303 has a pair of side-by-side chambers 311 and 312. Chambers 311 and 312 extend in a longitudinal direction and are located in a common horizontal plane. The chambers can be located in a common vertical plane whereby one chamber is positioned over the other chamber. A passage 313 connects chamber 311 with the tube 304. In a similar manner, a passage 314 connects chamber 312 with the tube 308.

A first plunger 316 is movably positioned in first chamber 311. A rearwardly directed rod 317 is attached to plunger 316. A second plunger 318 is movably located in chamber 312. A rod 319 is secured to the plunger 318 and extends in a rearward direction generally parallel to the rod 317. A trigger assembly or actuator indicated generally at 320 is mounted on the rear portion of the housing adjacent the rear end of rods 317 and 319.

Trigger assembly 320 has a lever 321. The midportion of lever 321 has a hole accommodating a transverse pivot pin 322. Pivot pin 322 is anchored in a downwardly extended handle or pistol grip 323 secured to the rear portion of the body 303. Lever 321 has a transverse head 324. A spring 325 engages the body 303 and upper end of lever 321 to bias the lever in the rear or cocked position. The forward portion of head 324 is in sliding engagement with the ends of rods 317 and 319.

Referring to FIGS. 29 and 30, head 324 has a longitudinal passage 326 for accommodating rod 319. A transverse bore 327 opens into passage 326. Slidably disposed in bore 327 is a pin 328. Pin 328 has a reduced diameter neck 329 attached to an enlarged head 331. A spring 332 engages the head 331 and a plug 333, closing the end of bore 327. Spring 332 biases the pin 328 into the passage 326. Rod 317 has a rearwardly directed finger 334. When rod 317 is in the rearward or cocked position, the finger 334 is located behind the head 331 and functions as a stop to prevent movement of pin 328 into passage 326.

Returning to FIG. 27, rod 317 has a notch or slot 336 in the upper portion thereof. The slot 336 cooperates with lock 337 to hold rod 317 in the dispensed or "in" position. Lock 337 comprises a movable pin 338 located in a passage surrounded by a boss 339. The pin 338 has a head 341 located above body 303 so that it can be gripped to release the lock. The forward portion of the pin carries a C-ring or clamp ring 342 providing a stop for a spring 343. Spring 343 is located concentrically around the pin and engages a portion of the body 303 to bias the pin 338 toward rod 317. When rod 317 has been moved to the in position, the pin 338 will be biased into the slot 336, thereby holding the pin in the in position. The rod 319 has a slot 344. A lock 346 on body 303 holds the pin in the in position. Lock 346 is identical to lock 337.

Returning to FIG. 30, when the lever 323 has been actuated, the rod 317 will be held in the in position by lock 337. Rod 319 is not moved because the head 324 will move relative to rod 319 as rod 319 moves through passageway 326. When the head 324 is returned by spring 325 to its initial rearward position, the pin 328 will be biased by spring 332 into passage 326. The second actuation or movement of the lever 321 toward the handle 323 will move the rod 319 in the forward direction.

Referring to FIG. 28, a first container or ampulla indicated generally at 350 is located in chamber 311. A forwardly directed needle 351 mounted on a transverse base 352 is located at the forward end of chamber 311. Needle 351 is a hollow member in fluid communication with passage 313.

A second container or ampulla, indicated generally at 353, is located in passage 312. The forward end of passage 312 has a longitudinally extended needle 354 mounted on a transverse base 356. Needle 354 is a hollow tubular member having a passage in fluid communication with the passage of the tube 314. The container 353 is an elongated cylindrical member of glass, plastic or the like having a head 357. The head has a rubber plug (not shown) in alignment with needle 354. Slidably positioned within the container is a plunger of piston 358 confining fluid 359 in the container. The plunger 318 is slidably positioned within the container and engageable with the piston 358. On movement of plunger 318 in the forward direction, head 357 will be driven through needle 354, thereby providing a fluid communication between the chamber of the container 353 and tube 314. The piston 358 will be moved in a forward direction to drive the fluid from the container. The fluid can be a drug, tissue adhesive, or semi-fluid material for treating and occluding the canals of the Fallopian tubes.

Container 350, shown in FIG. 31, has a cylinder 361 for storing fluid 362, as drugs, water or the like. The forward end of cylinder 361 has a head 363 having a passage closed with a plug 364. The open end of cylinder 361 is closed with a plunger 366 carrying a piston 367. The rear portion of plunger 366 has an outwardly directed flange 368 engageable with a spring 369. The forward end of spring 369 engages an annular seat 371 on the cylinder 361 to bias the plunger 366 in an outward direction or out of cylinder 361. Plunger 366 has a central longitudinal bore 372 slidably accommodating an actuator rod 373. Rod 373 has an axial bore accommodating a compression spring 374 to provide a yieldable link between rod 373 and plunger 366.

Plunger 316 attached to rod 317 engages the end of rod 376. On movement of plunger 316 in the forward direction, spring 374 will be initially compressed applying a uniform pressure on plunger 366. The cylinder 361 will be moved in a forward direction whereby needle 351 will pierce plug 364, providing fluid communication between the container and passage 313. The continued movement of the plunger 316 will drive the piston 367 toward the plug 364, thereby dispensing the fluid from cylinder 361. The dispensed fluid will flow through tube 304 and into sleeve member 305 via holes 307 to expand sleeve member 305, as shown in broken lines in FIG. 22. Sleeve member 305 will expand with a uniform pressure so as to fill the uterine cavity and exert uniform pressure on the inside wall of the cavity. The pressure of sleeve member 305 on the cavity wall will be uniform regardless of the size of the uterine cavity.

Body 303 has doors or closure members closing openings into the chambers 311 and 312 whereby the containers 350 and 353 can be removed and replaced. Other types of containers, as disclosed herein, can be inserted into the chambers.

In use, the dispensing catheter performs a method of introducing a material, as a drug, tissue adhesive, contraceptive gel or like material, into the canals of the Fallopian tubes. The method includes the introduction of an elongated catheter 302, with sleeve member 305 in the contracted position, through the cervical opening into the uterine cavity. Sleeve member 305 is expanded with fluid under pressure to fill the uterine cavity and apply uniform pressure on the inside of the uterine wall. The fluid under pressure is delivered to sleeve member 305 via the passage in the tube 304. Actuator 320 is moved in a forward direction to force plunger 316 in a direction to move the container 350 into operative engagement with needle 351. Needle 351 will puncture the plug 364, whereby the fluid 362 will flow via the passage in tube 304 to expand sleeve member 305. The sleeve member, being a sheet of flexible, elastic rubber or similar material, has a low surface tension and applies a uniform expansion force to the inside of the uterine wall. This effects a relatively tight seal and fit, enabling the same catheter construction to be used on all types of primate female, regardless of the size of the uterine cavity.

The material under pressure is then dispensed into the uterine cavity between the expanded sleeve member and the fundus of the uterus. The material, being under pressure, moves toward and into the canals of the Fallopian tubes. The expanded sleeve member, being located against the fundus wall, aids the movement of the material toward the canals of the Fallopian tubes. The material can be a fluid tissue adhesive which will flow into the canals. The moisture in the tissue of the canals will polymerize or set the tissue adhesive and thereby block or occlude the canals. The fluid confined by the sleeve member is drained to contract the sleeve member. The catheter is then withdrawn from the uterine cavity.

Figure 32:
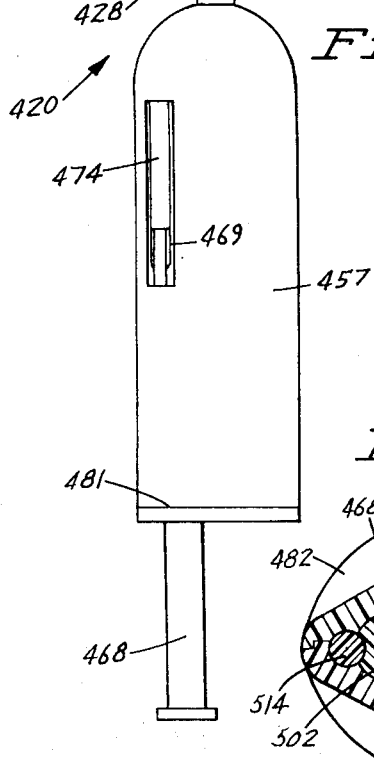
FIG. 32 is a foreshortened sectional view of a reproductive system of a female accommodating a dispensing instrument of the invention for locating drug material in both canals of the Fallopian tubes.
Figure 34:
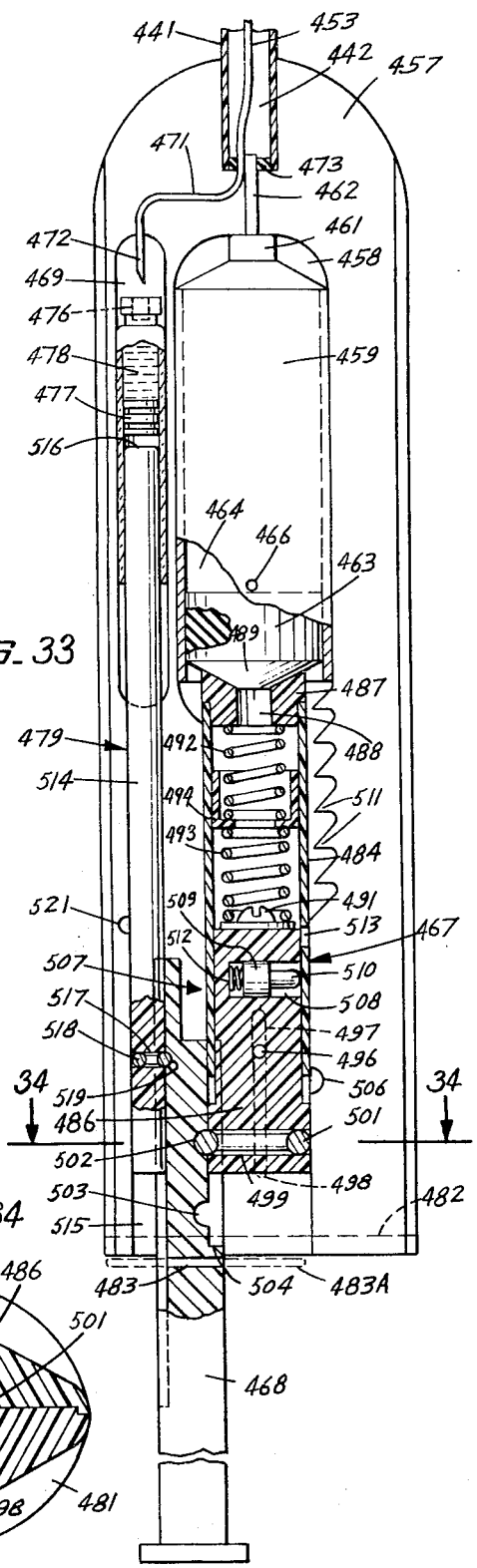
FIG. 34 is a sectional view taken along the line 34—34 of FIG. 33.

Referring to FIG. 32, there is shown the dispensing instrument indicated generally at 420 with the probe located in the uterine cavity. The female reproductive system shown generally at 421 has a uterus 422 joined to a pair of Fallopian tubes 423 and 424. The lower part of uterus 422 is integral with an elongated vagina 426. Vagina 426 has a vaginal cavity 427 having an opening or entrance 428. The opposite end of vaginal cavity 427 is in communication with the cervix 429. Cervix 429 has a cervical opening 431 providing a passage from vaginal cavity 427 to uterine cavity 432. Fallopian tubes 423 and 424 have exits 433A and 434A at opposite sides of the upper part of the uterine cavity 432.

The uterus 422 is a generally pear-shaped, thick walled, hollow organ situated between the bladder and rectum. The uteri of females vary in size and shape. Wall thickness, wall strength and sensitivity to pain may vary from female to female. The size and configuration of the uterine cavities can vary. The uterine cavity 432 is generally flattened and triangular in shape. Some uteri have cavities that have other shapes.

The Fallopian tubes 423 and 424 are paired, trumpet-shaped muscular members about 12 cm. in length which extend from the superior angles of the uterine cavity 432 to the ovaries (not shown). The outlets 433A and 434A of canals 433 and 434, respectively, can vary in positon relative to the uterine cavity and relative to each other. Outlets 433A and 434A are usually symmetrically opposite each other, as shown in FIG. 32, and their position and proximity are principally related to the uterine size and configuration. Also, the size of the canals 433 and 434 and the size of outlets 433A and 434A vary from female to female.

Fallopian tubes are commonly divided into isthmus, intramural and ampullary sections. Canals 433 and 434 provide passages for the movement of ova from the ovaries to the uterine cavity 432 as well as the movement of sperm from the uterine cavity toward the ovaries. The intramural sections of the Fallopian tubes traverse the uterine wall generally in a more or less straight fashion, but their course may be tortuous in some females. The walls of the Fallopian tubes consist of three layers; the serosal layer, the muscular layer and the mucosal lining.

Uterus 422 has a top wall or fundus 436 and side walls 437 and 438 which surround the uterine cavity 432. The inside of top wall 436 and the insides of side walls 437 and 438 have an inside lining or membrane 439 which is periodically sloughed off in the normal cycle of the female.

Dispensing instrument 420 has an elongated probe or tubular member 411 having a length sufficient to pass through the vaginal cavity 427 and into uterine cavity 432. Member 441 has a longitudinal passage 442 extended throughout its length. A balloon assembly indicated generally at 443 is mounted on the upper or outer end of tubular member 441. Balloon assembly 443 has a flexible and expandable sleeve member 444 surrounding the upper end of probe 441. A fastener 446, as a collar or thread, attaches the upper end of sleeve 444 to probe 441. A similar fastener 447 attaches the opposite end of sleeve 444 to the probe 441. Probe 441 has a plurality of openings 448 which provide communication between the passage 442 and a chamber 449 within sleeve member 444.

Sleeve member 444 is a tubular sheet member of soft and relaxed, flexible and elastic material, as rubber or plastic, which expands with a miimum of tension. For example, thin latex rubber having low surface tension is suitable material for sleeve member 444. The low surface tension of the rubber allows the rubber to uniformly expand with relatively low pressure. The material of sleeve member 444 readily expands to displace uterine cavity 432 by conforming to the shape of the uterine cavity without applying extreme pressure to localized portions of the uterus walls 437 and 438. When cavity 432 is fully displaced with sleeve member 444, as shown in FIG. 36, sleeve member 444 is in uniform surface engagement with the inside lining 439. Conventional balloon catheters, being of hard, relatively non-elastic material, do not assume the configuration of the uterine cavity when expanded.

The upper or outer end of probe 441 is closed with a head 451. Head 451 has a transverse passage 452 open to opposite sides of head 451. An elongated tube 453 is secured to the head 451. Tube 453 extends the length of probe 441 and has a passage 454 for carrying a drug material to the transverse passage 452 which directs the drug material in opposite directions in two portions into the upper section of the uterine cavity 432. Head 451 has a longitudinal section or cap 456 having a top surface or wall adapted to engage the inner wall of fundus 436. The cap 456 spaces the passage 452 from the inner wall of fundus 436.

Figure 33:
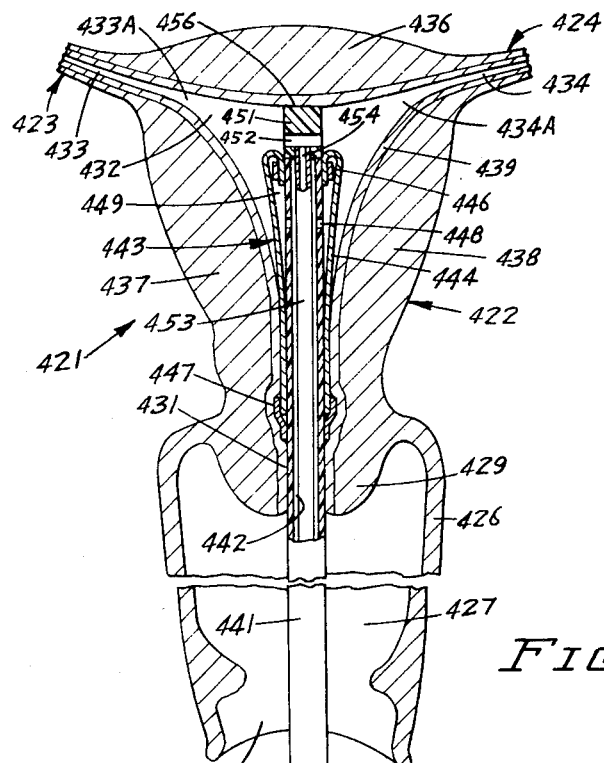
FIG. 33 is a longitudinal sectional view of the dispensing assembly of the instrument of FIG. 32.

Referring to FIG. 33, dispensing instrument 420 has an elongated housing or body 457 attached to the end of probe 441. Body 457 has a first chamber 458 accommodating an elongated cylinder 459. Cylinder 459 has a forwardly directed neck 461 connected to a tube 462.

Tube 462 has a passage which is in communication with passage 442 of the probe 441 so that fluid, as air, in cylinder 459 can flow via passage 442 into chamber 449 of the balloon assembly and thereby expand the sleeve member 444. The open end of cylinder 459 is closed with a piston 463 to trap the fluid in chamber 464. The cylinder 459 has a hole 466 adjacent the piston 463 to allow air and sterilizing gases to flow into the chamber 464.

Located rearwardly of the piston 463 is a first drive assembly indicated generally at 467 operable to move the piston 463 into cylinder 459. The first drive assembly 467 is connected to an actuator 468 projected rearwardly from body 457.

Body 457 has a second chamber 469 located adjacent one side of the first chamber 458. A tube 471 is mounted in the body 457 to connect the tube 453 to chamber 469. Tube 471 has a longitudinally extended needle 472 projected into chamber 469. The opposite end of tube 471 is mounted in a plug 473 closing the end of probe 441 and connected to the tube 453 which leads to head 451. Chamber 469 has an elongated shape and is open to the top of body 457, as shown in FIG. 32. A cylindrical container or ampulla 474 is located in chamber 469 in alignment with needle 472. The forward end of container 474 has a pierceable plug 476 aligned with needle 472. The open end of container 474 is closed with a slidable piston 477 to trap drug material 478 in container 474.

A second drive assembly indicated generally at 479 extends rearwardly form container 474 and is drivably connected to actuator 468. Actuator 468 is operable to complete the entire dispensing of drug material into the canals of the Fallopian tubes in a single stroke. The rear portion of housing 457 has outwardly and oppositely directed flanges 481 and 482 which serve as finger grips during actuation of actuator 468. Actuator 468 has a hole 483 for accommodating a pin 483A to hold the actuator 468 in the operative position. The pin 483A prevents accidental actuation of the dispensing instrument.

Drive assembly 467 is a force-transmitting mechanism operable to move piston 463 into cylinder 459 and thereby increase the pressure in the fluid system for the balloon assembly 443 and expand sleeve member 444. Drive assembly 467 has a cylinder or sleeve 484 slidably carrying a body 486. The opposite or upper end of sleeve 484 is attached to a head 487. Head 487 has a central hole 488 which provides access into sleeve 484. The outer end of piston 463 has a cone-shaped portion 489 to accommodate the cone-shaped outer end of head 487. The hole 488 is aligned with an adjusting screw 491 threaded into body 486. The position of screw 491 relative to body 486 can be changed with the use of a tool, as a screwdriver, extended through hole 488. A pair of springs 492 and 493 bias the sleeve 484 and body 486 in opposite directions whereby the first drive assembly 467 is biased into its elongated position. Spring 492 abuts against head 487. Spring 493 rests on screw 491. Adjusting the positon of screw 491 adjusts the tension or force of the spring 493 which biases the head 487 and body 486 in opposite directions. Screw 491 performs a fine adjustment of the spring force to accommodate variations in spring 493 and to provide for desired fluid pressure in chamber 449. A washer 494 having a central hole for rod 488 is located between springs 492 and 493. Spring 492 is a light or weak spring as compared to spring 493. The weak spring 492 will compress under a light load, for example 2–3 psi, whereby the washer 494 will abut against head 487. This insures the partial expansion of sleeve member 444 at low predetermined maximum pressure. The predetermined maximum pressure is determined by the compression force characteristics of spring 493 and permits the instrument to be used with all shapes and sizes of uteri, as the spring 493 adjusts for the differences in the uteri.

Sleeve 484 and body 486 are held in assembled relation with a pin 496 extended through elongated longitudinal slot 497 in sleeve 484. Slot 497 permits the sleeve 484 to move relative to body 486 as the springs 492 and 493 are compressed. Pin 496 projects through slot 497 into an elongated linear groove 498 in the housing 457 and thereby prevents rotational movement of the drive assembly 467 relative to housing 457.

Body 486 has a transverse passage 499 accommodating a drive link 501. The drive link 501 has spherical members at its opposite ends joined with a transverse member or tube. The first end of drive link 501 is located in a recess 502 in the side of actuator 468. Actuator 468 has a second recess 503 for accommodating the link 501. Located below recess 503 is a shoulder 504 adapted to engage the end of body 486 when link 501 is in recess 503. Housing 457 has a recess 506 adapted to accommodate the opposite or right end of drive link 501. Recess 506 is located in a forward direction from the initial position of drive link 501, as shown in FIG. 33, so that the actuation of drive assembly 467 is temporarily halted or interrupted until the end of body 486 engages the shoulder 504, at which time the movement of the drive assembly 467 is continued. The locations of recesses 506 and 521 in housing 457 can be coordinated with each other so that the initial expansion of sleeve member 444 overlaps the discharge of drug material into the uterine cavity and the continued expansion of sleeve member 444. In this case, sleeve member 444 has a continuous expansion until the sleeve member 444 has been subjected to the maximum fluid pressure.

A lock unit indicated generally at 507 is movably located in a bore 508 in body 486. Lock unit 507 has a plunger 509 carrying an outwardly directed finger or projection 510. Finger 510 is adapted to engage one of a plurality of teeth 511 located in housing 457. The teeth 511 face drive assembly 467. Teeth 511 are ratchet teeth which allow only reverse movement of the drive assembly when lock unit 507 is in operation position with teeth 511. Plunger 509 is biased in an outward direction with a spring 512 located at the base of bore 508. Sleeve 484 has a hole 513 spaced forwardly from finger 510. On compression of springs 492 and 493, the body 486 moves relative to sleeve 484 until the finger 510 is aligned with hole 513, at which time spring 512 will bias finger 510 through hole 513 into engagement with one of the teeth 511. This prevents further movement of the drive assembly 467 in a forward direction and limits the pressure of the fluid in the chamber 449 of sleeve 444.

The second drive assembly 479 is operable to drive the container 474 onto needle 472 and force piston 477 into the container and thereby drive the drug material 478 through needle 472 into tube 453. Tube 453 carries the fluid to head 451 where it is discharged in opposite directions into the upper portion of uterine cavity 432. Returning to FIG. 2, second drive assembly 479 has an elongated linear plunger 514 slidably located in a longitudinal passage 515 in housing 457. Plunger 514 has a forward end 516 adapted to engage piston 477. The opposite end of plunger 514 has a transverse passage 517. A movable drive link 518 is located in passage 517. Link 518 has spherical ends that are connected with a rigid member such as a tube. One end of drive link 518 is located in a semispherical recess 519 located in the side of actuator 468. The opposite end of drive link 518 rides on the side wall of the housing 457 forming part of passage 515, thereby retaining the link in recess 519. Housing 457 has a recess 521 forward of the link 518 so that the link 518 will remain in driving relationship with actuator 468 until the link is aligned with recess 521. At this time the link 518 will be forced into recess 521 whereby actuator 468 will continue to move in a forward direction and plunger 514 will remain stationary.

In use, the dispensing instrument 420 is packaged with container 474 located in chamber 469. Actuator 468 is locked in an inoperative position with a pin 483A extended through hole 483. Pin 483A engages the end of housing 457 to prevent actuator 468 from moving into the housing. The entire dispensing instrument is sterilized before it is used.

The operating procedure begins with inserting the balloon assembly 443 into the vaginal cavity 427, through cervical opening 431 and into uterine cavity 432, as shown in FIG. 32. Sleeve member 444 is in the collapsed condition so that the balloon assembly can be readily positioned in the uterine cavity. The probe 441 is moved into the uterine cavity until head 451 engages the fundus 436. It is known that uteri can vary in size, shape and position so that the balloon assembly may or may not be symmetrically located relative to the Fallopian tubes 423 and 424. As shown in FIG. 32, balloon assembly 443 is centrally located in the uterine cavity 432. In some cases, the balloon assembly may be angularly positioned in the uterine cavity adjacent one side of the cavity. Dispensing instrument 420 is effective in placing drug material into both canals of the Fallopian tubes regardless of the position of the balloon assembly in uterine cavity 432.

Pin 483A is removed from hole 483, making plunger 468 ready to be moved into the housing 457 to inflate the expandable sleeve member 444 and dispense drug material into uterine cavity 432 and then fully expand the sleeve member 444 to pump or force the drug material into the canals of the Fallopian tubes. The operator uses flanges 481 and 482 as finger rests so that inwardly directed force can be applied to the actuator 468. As shown in FIG. 35, the actuator 468 has been moved into housing 457 a short distance such that the first drive assembly has moved the piston 463 into cylinder 59. This expands sleeve member 444 so that it forms a plug or seal in the lower portion of the uterine cavity 432. Sleeve member 444 is expanded into firm engagement with the inside lining or membrame 439. Drive link 501 couples actuator 468 to the first drive assembly 467 to transmit the motion of actuator 468 to the first drive assembly 467. This moves piston 463 into chamber 464. The drive link 518 couples plunger 514 with actuator 468 so that athe forward end 516 of the actuator engages piston 477 in the container 474. This moves the entire container 474 in a forward direction. The needle 472 pierces plug 476, thereby moving the needle through plug 476 and into the chamber containing the drug material 478. The drive link 101 is aligned with recess 506 in the housing 457. This permits the drive link 501 to move to the right, as shown in FIG. 35, releasing the drive link from the actuator 468. The continued movement of the actuator 468 applies force to plunger 416 which moves piston 477 into container 474. Drug material 478 is forced via tubes 471 and 453 to head 451. The drug material is discharged in opposite directions via the transverse passage 452 into the upper part of uterine cavity 432.

As shown in FIG. 36, the continued movement of actuator 468 places the shoulder 504 in engagement with the bottom of body 486. At the same time drive link 501 moves into recess 503, thereby releasing drive link 501 from recess 506. Actuator 468 is moved into housing 457, thereby increasing the pressure in chamber 464. This further expands sleeve member 444. The expanding sleeve member 444 drives the drug material from the upper portion of the uterine cavity through exit openings 433A and 434A of the canals 433 and 434 of the Fallopian tubes. The sleeve member 444 continues to expand until the fluid pressure in the system containing the sleeve member and chambers 449 and 464 is approximately 8 psi. Other pressures can be selected as the upper pressure limit. This pressure is determined by the compression characteristics of the springs 492 and 493 and adjusting screw 491. The compression of springs 492 and 493 permits body 486 to move into sleeve 484. This movement continues until finger 510 is aligned with opening 513. When finger 510 and hole 513 are aligned, the spring 512 forces finger 510 through hole 513 and into the space between adjacent teeth 511. Finger 510 anchors on a forward tooth, thereby preventing further movement of the actuator 468 into housing 457. Since actuator 468 is prevented from moving into the housing 457 by lock unit 507, the pressure in the balloon chamber 449 is limited to a selected maximum pressure, depending on the compression characteristics of springs 492 and 493.

As the actuator 468 is moved into housing 457 from the position shown in FIG. 35 to the position shown in FIG. 36, drive link 518 moves from recess 519 into recess 521. This terminates the forward motion of plunger 514 to stop dispensing the drug material into uterine cavity 432. The continued movement of actuator 468 increases the fluid pressure in the chamber 449, thereby expanding sleeve member 444 to pump or push the drug material from uterine cavity 432 into canals 433 and 434 of the Fallopian tubes. The pumping action ceases when the sleeve member 444 is fully expanded, as shown in FIG. 36. This locates the drug material in the Fallopian tubes as the pumping force applied to the drug material is insufficient to move the drug material through the Fallopian tubes into the body cavity.

The actuator 468 is then pulled out of housing 457. Drive link 501, being located in recess 503, provides a drive connection between body 486 and plunger 468. Finger 510 of lock unit 507 slips over teeth 511. This pulls the piston 463 out of chamber 464. The fluid in chamber 449 flows back into chamber 464, contracting sleeve member 444. This releases sleeve member 444 from engagement with lining 439 and enables balloon assembly 443 to be withdrawn from the uterus of the patient.

When drug materials of the cyanoacrylate tissue adhesive type are used, canals 433 and 434 will be permanently occluded. Tissue adhesives, as the cyanoacrylate type, cause fibroblastic proliferation which in time closes the canals 433 and 434. The tissue adhesives polymerize when exposed to a hydroxyl ion source, such as water. The cells adjacent the adhesive are damaged and are eventually replaced with fibrous tissue. Certain other tissue adhesives will polymerize in response to body heat or other stimuli.

In terms of method, the dispensing instrument is used to place drug material in both canals of the Fallopian tubes via the uterine cavity. The contracted balloon assembly is initially placed in the uterine cavity, as shown in FIG. 32, by inserting the balloon assembly 443 through cervical opening 431. The actuator 468 is then released so that it can be moved into housing 457. The operator moves the single actuator 468 with a continuous movement into housing 457 to complete the operation. The first drive assembly 467 and second drive assembly 479 are coordinated to sequentially operate to partially expand the sleeve member 444 to displace the lower portion of the uterine cavity and form a seal with the lower walls of the uterine cavity. The plunger 514 then engages the piston 477 to force the container onto needle 472 and force drug material 478 from the container and discharge the drug material in opposite directions into the uterine cavity 432 above the partially expanded sleeve member 444. This operation is shown in FIG. 35. The continued movement of actuator 468 further expands the partially expanded sleeve member 444 to fully displace uterine cavity 432. This is done by subjecting the sleeve member 444 to fluid under pressure by moving the piston 463 into chamber 464. The actuator 468 will continue to move until lock unit 507 engages one of the teeth 511, thereby preventing further expansion of the sleeve member 444. The sleeve member 444 can only be subjected to a maximum predetermined pressure so as not to place undue pressure on the walls of the uterus. The expanding sleeve member 444 forces or pumps the drug material that has been discharged into the uterine cavity through the openings 433A and 434A and into canals 433 and 434 of the Fallopian tubes. Sleeve member 444 is then contracted by relieving the pressure applied thereto. This is done by pulling actuator 468 out of housing 457 so that the fluid can move into container chamber 464. The instrument is then removed from the uterine cavity via the cervical opening and vaginal passage.

The drug material can be one of a number of fluids or semi-fluids used to test, treat or occlude the canals of the Fallopian tubes. For example, the drug material can be a tissue adhesive. The tissue adhesive can be a cyanoacrylate-type material or like material used as surgical glue. Cyanoacrylate is a liquid plastic which sets up or polymerizes in response to moisture and thereby functions to occlude the canals of the Fallopian tubes. The cyanoacrylates include, but are not limited to, methyl cyanoacrylate, methyl-2-cyanoacrylate, ethyl cyanoacrylates, n-propyl cyanoacrylates, n-butyl cyanoacrylates, n-amyl cyanoacrylates, n-hexyl cyanoacrylates, n-heptyl cyanoacrylates, isobutyl-2-cyanoacrylates and n-octyl cyanoacrylates. The drug material can also be of a type that sets up in response to body heat or other stimuli. It may be a type which produces permanent occlusion or of a type which will temporarily block or occlude the canals of the Fallopian tubes, after which the canals will be reopened and resume their normal function. Examples of other types of drug materials are contraceptive gels, water, silicone elastomers, formaldehyde-type materials and like materials.

Referring to FIGS. 37 and 38, there is shown a modification of the dispensing instrument indicated generally at 420A. Dispensing instrument 420A and the female reproductive system associated therewith follow the dispensing instrument shown in FIGS. 32–36. Corresponding parts of the instrument and reproductive system have the same reference numerals with the suffix A.

Dispensing instrument 420A uses a two-part drug material which is mixed at the end of the probe as it is forced into the upper part of the uterine cavity 432A. The mixed drug material of the sleeve member 444A to displace uterine cavity 432A.

Head 651 is mounted on the outer end of the probe or tubular member 441A. The head 651 has a transverse passage 652 having oppositely directed discharge openings for directing the drug material in two parts into the upper part of the uterine cavity 432A. A first tube 653 and a second tube 654 are connected to the head 651. The head has a mixing chamber or passage 655 in fluid communication with the passages of tubes 653 and 654 and the transverse passage 652. The drug materials flow through the tubes 653 and 654 and are mixed in chamber 655. The mixing continues as the drug materials are separated and forced in opposite directions in passage 652, as indicated by the arrows.

Housing 457A has a pair of chambers 656 located adjacent chamber 458A for accommodating a pair of ampullae or containers 657 and 659. Container 657 stores a first drug material 658. Container 659 stores a second drug material 660. A first piston 661 is slidably located in container 657. In a similar manner, a piston 662 is slidably located in container 659. Plunger 514A of the second drive assembly 479A has a bifurcated end forming a pair of fingers 663 and 664. Finger 663 is positioned in container 657 and engages piston 661. Finger 664 is located in container 659 and engages piston 662. The tubes 653 and 654 extend into housing 457A and terminate in needles 666 and 667. Needles 666 and 667 are in alignment with the pierceable end portions of containers 657 and 659.

On actuation of single actuator 468A, the first drive assembly 467A will operate to initially expand the sleeve member 444A to fill and seal the lower portion of the uterine cavity 432A. Continued movement of actuator 468A will engage the second drive assembly 479A to move the fingers 663 and 664. Plunger 514A moves in a forward or upward direction, as shown in FIG. 6, to drive the containers 657 and 659 onto needles 666 and 667, respectively. Fingers 663 and 664, being in engagement with pistons 661 and 662, simultaneously force the drug materials 658 and 660 through the tubes 654 and 653. The drug materials are simultaneously discharged into the mixing chamber 655. Substantially the same amounts of drug materials are introduced into the mixing chamber 655 so that the mixture of drug materials contains about 50 per cent of the first drug and 50 per cent of the second drug material. The mixed drug material, indicated at 668 in FIG. 37, is introduced into the upper part of uterine cavity 432A. The mixed drug material 668 flows in opposite directions in substantially equal amounts. The flow is continuous until plunger 414A has reached the end of its stroke. At this time, the continuous movement of the actuator 468A further expands the sleeve member 434A forcing the mixed drug material into the canals 433A and 434A of the Fallopian tubes. Drug materials 658 and 660 can be the type which when mixed will set up to form a sem-rigid plastic material. The mixture can be responsive to moisture in the tissues to set up or responsive to body heat or other factors to set up. The mixture has a reaction time such that it can be introduced into canals 433A and 434A before it will set up. The following is an example of the materials of the two-part drug material. The two-part drug materials may be two-part epoxies, two-part tissue adhesives, silicone RTV, or a polymer consisting of Dow Corning Silastic 382 Medical Elastomer and 360 Medical Fluid. It is understood that other types of drug materials that are mixed and set up can be used. Furthermore, the ratio of the drug material can be varied by increasing the size of one of the containers. For example, two parts of the first drug material can be mixed with one part of the second drug material by using the appropriate size containers in the housing 457A.

The drug material can be a contraceptive drug for local action in the Fallopian tubes and uterus. For example, bioabsorbable microspherules having contraceptive drugs, as progestins, can be delivered to the canals of the Fallopian tubes. The microspherules break down over a period of time, i.e., one year, thereby inhibiting conception during this period.

Biologicals, as fibrinolytic enzymes, can be introduced into the canals of the Fallopian tubes and uterine cavity to treat the tissues. The biologicals are used to treat inflammation and prevent adhesions from forming around the ends of the Fallopian tubes.

Diagnostic materials can be introduced into the canals of the Fallopian tubes with the apparatus and method of the invention. These materials include oil base and aqueous base X-ray dyes and color indicator dyes, as methylene blue and indigo carmine and the like.

Anesthetic materials can be introduced into the canals of the Fallopian tubes with the apparatus of the invention.

The drug material can be of the type which treats the canals and uterus to enhance the flow of ova and sperm in the canal and uterus. The drug material can include material which expands or opens the canals or passages of the Fallopian tubes to enhance fertilization or conception. At the present time there are several materials or chemicals which are used to treat the canals of the Fallopian tubes to enhance fertilization or conception. Anti-inflammatory agents, as cordocoids, can be used to locally treat inflammation. Antibiotics can also be used for local treatment of the Fallopian tubes.

It is believed that in some cases of infertility the sperm are blocked or unable to transport themselves across the cervix and endometrial cavity. The apparatus and method of the invention is usable to deliver sperm into the uterine cavity and canals of the Fallopian tubes to enhance conception.

While there have been shown and described preferred embodiments of the dispensing instrument and method of introducing materials into both canals of the Fallopian tubes of a female, it is understood that various changes in the structure and method may be made by those skilled in the art without departing from the spirit of the invention.

The embodiments of the invention in which an exclusive property or privilege is claimed are defined as follows:

1. An instrument for use in performing female sterilization comprising: means for containing material for occluding the canals of the Fallopian tubes, dispensing means having a first portion positionable in the uterine cavity of the femal and operable to move the material from the means for containing material to the uterine cavity and a second portion operable to rapidly move the material from the uterine cavity into the canals of the Fallopian tubes, and control means connected to the first and second portions for automatically rapidly operating the second portion and for automatically operating the first portion to move material into the uterine cavity before operation of the second portion is completed.

2. The instrument of claim 1 wherein: said dispensing second portion an expandable means positionable in the uterine cavity of a female and means operable to rapidly expand the expandable means in the uterine cavity.

3. The instrument of claim 2 wherein: the expandable means is an expandable tubular sheet member.

4. An apparatus for introducing a fluid into the canals of the Fallopian tubes from the uterine cavity of the uterus comprising: means having an expandable member positionable in the uterine cavity and a stop member locating the expandable member in the uterine cavity in a position spaced from the top inside wall of the uterus, means operable to expand the expandable member to hold the expanded member in engagement with the side inside walls of the uterus and spaced from the top inside wall of the uterus, means for dispensing a first fluid into the uterine cavity between the expanded member and the top inside wall, said first fluid being directed into the canals, and means for dispensing a second fluid into the uterine cavity between the expanded member and the top inside wall, said second fluid forcing the first fluid into the canals.

5. The apparatus of claim 4 wherein: the means operable to expand the expandable member include means to supply a fluid under pressure to the expandable member.

6. The apparatus of claim 4 wherein: the means having an expandable member includes an elongated tubular member and means mounting the expandable member on one end portion of the tubular member, said stop member being mounted on the tubular member.

7. An instrument for placing material into both canals of the Fallopian tubes open to the uterine cavity comprising: expandable sleeve means surrounding a chamber for displacing the uterine cavity, dispenser means connected to said sleeve means operable to partly expand the sleeve means, discharge material into the uterine cavity above the partly expanded sleeve means, and fully expand the sleeve means to force the material in the uterine cavity into the canals of the Fallopian tubes, said dispenser means having first means to supply fluid under pressure to said chamber to expand the sleeve means, second means operable to discharge material into the uterine cavity, and an actuator operably connected to the first means and the second means, said actuator continuously movable to operate the first means to partly expand the sleeve means, operate the second means to discharge material into the uterine cavity above the partly expanded sleeve means, and further operate the first means to fully expand the sleeve means to move the material from the uterine cavity into the canals of the Fallopian tubes.

8. The instrument of claim 7 wherein: the sleeve means is an expandable tubular sheet material having low surface tension properties.

9. The instrument of claim 7 including: a tubular member connected to the dispensing means, means mounting the sleeve means on the tubular member, head means having side material discharge openings on the forward end of the tubular member to direct material into the uterine cavity.

10. The instrument of claim 9 wherein: said head means includes an enlarged portion adapted to contact the fundus and space the discharge openings from the fundus.

11. The instrument of claim 7 wherein: the first means includes a cylinder and piston movable relative to the cylinder to supply fluid under pressure to the chamber to expand the sleeve means, and a first drive assembly operably coupled to the actuator and cooperating with the piston to move the piston relative to the cylinder in response to movement of the actuator.

12. The instrument of claim 11 including: lock means associated with the first drive assembly to stop movement of the drive assembly when a predetermined fluid pressure is present in the chamber surrounded by the sleeve means.

13. The instrument of claim 11 wherein: the first drive assembly includes a first member, a second member movable relative to the first member, and biasing means holding the members in an extended position.

14. The instrument of claim 13 including: means acting on the biasing means to change the biasing force of the biasing means.

15. The instrument of claim 13 including: lock means cooperating with said members and dispensing means when the members are in a contracted position relative to each other to prevent movement of the drive assembly in the direction to increase fluid pressure to thereby limit the fluid pressure applied to the sleeve means.

16. The instrument of claim 11 wherein: the dispensing means includes a housing, said housing having a plurality of teeth facing the first drive assembly, said drive assembly having lock means engageable with one of the teeth to stop movement of the drive assembly when a predetermined fluid pressure is present in the chamber surrounding the sleeve means.

17. The instrument of claim 16 wherein: the lock means includes a body having a projection, and biasing means for moving the projection between adjacent teeth when the predetermined pressure is attained.

18. The instrument of claim 7 including: first releasable means to drivably connect the actuator with the first means and second releasable means to drivably connect the second means to the actuator.

19. The instrument of claim 18 wherein: said first releasable means includes a movable means mounted on the first means and engageable with the actuator to drivably connect the actuator to the first means.

20. The instrument of claim 18 wherein: said second releasable means includes a movable means mounted in the second means and engageable with the actuator to drivably connect the actuator to the second means.

21. The instrument of claim 7 wherein: the second means includes a container means for storing the material, means for carrying the material from the container means to the uterine cavity, and plunger means cooperating with the container means and drivably connected to the actuator whereby movement of the actuator drives material from the container means to the uterine cavity.

22. The instrument of claim 21 including: releasable means including a movable means mounted in said plunger means and engageable with the actuator to drivably connect the actuator to the plunger means.

23. The instrument of claim 7 wherein: the dispenser means includes a housing having a first chamber for the first means and a second chamber for the second means and means to slidably mount the actuator between said chambers.

24. The instrument of claim 23 including: first movable means mounted in the first means and engageable with the actuator to drivably connect the actuator to the first means, said housing having a first recess to accommodate a part of the first movable means to release the drive connection between the first movable means and the actuator, second movable means mounted in the second means and engageable with the actuator to drivably connect the actuator to the second means, said housing having a second recess to accommodate a part of the second movable means to release the drive connection between the second movable means and the actuator after the drive connection between the first movable means and the actuator has been released.

25. The instrument of claim 24 wherein: said first means and second means each have passages accommodating the movable means associated therewith.

26. The instrument of claim 7 including: head means located adjacent the forward portion of the sleeve means, said head means having passage means for receiving a plurality of drug materials whereby the drug materials are mixed in the passage means and discharged into the uterine cavity.

27. The instrument of claim 7 wherein: the second means includes a first container means for storing a first material and a second container means for storing a second material, means for carrying the first material and second material and mixing said materials from the first and second container means to the uterine cavity, and plunger means cooperating with the first container means and second container means and drivably connected to the actuator whereby movement of the actuator drives the first and second material from the respective container means to the uterine cavity.

28. An instrument for placing material into both canals of the Fallopian tubes open to the uterine cavity comprising: expandable sleeve means surrounding a chamber for displacing the uterine cavity, dispensing means connected to said sleeve means operable to partly expand the sleeve means, discharge material into the uterine cavity above the partly expanded sleeve means, and fully expand the sleeve means to force the material in the uterine cavity into the canals of the Fallopian tubes, said dispensing means including a single actuator continuously movable to partly expand the sleeve means, discharge material into the uterine cavity above the partly expanded sleeve means and fully expand the sleeve means to move the material from the uterine cavity into the canals of the Fallopian tubes.

29. The instrument of claim 28 wherein: the sleeve means is an expandable tubular sheet material having low surface tension properties.

30. The instrument of claim 28 including: a tubular member connected to the dispensing means, means mounting the sleeve means on the tubular member, head means having side material discharge openings on the forward end of the tubular member to direct material into the uterine cavity.

31. The instrument of claim 30 wherein: said head means includes an enlarged portion adapted to contact the fundus and space the discharge openings from the fundus.

32. The instrument of claim 28 wherein: the first means includes a first drive assembly operably coupled to the actuator and movable in response to movement of the actuator to supply fluid under pressure to the chamber surrounded by the sleeve means whereby the sleeve means expands to displace the uterine cavity.

33. The instrument of claim 32 including: lock means associated with the first drive assembly to stop the movement of the drive assembly when a predetermined fluid pressure is present in the chamber surrounded by the sleeve means.

34. The instrument of claim 32 wherein: the dispensing means includes a housing, said housing having a plurality of teeth facing the first drive assembly, said drive assembly having lock means engageable with one of the teeth to stop movement of the drive assembly when a predetermined fluid pressure is present in the chamber surrounding the sleeve means.

35. The instrument of claim 32 including: first releasable means to drivably connect the actuator with the first drive assembly.

36. The instrument of claim 35 wherein: the first releasable means includes a movable means mounted in the first drive assembly and engageable with the actuator to drivably connect the actuator with the first drive assembly.

37. The instrument of claim 28 including: a container for storing the material, means for carrying the material from the container to the uterine cavity, and plunger means cooperating with the container and drivably connected to the actuator whereby movement of the actuator drives the material from the container to the uterine cavity.

38. The instrument of claim 37 including: second releasable means including a movable means mounted on said plunger means and engageable with said actuator to drivably connect the actuator to the plunger means.

39. The instrument of claim 28 including: a first container for storing a first material and a second container for storing a second material, means for carrying the first material and the second material and mixing said materials from the first and second containers to the uterine cavity, and plunger means cooperating with the first container and second container and drivably connected to the actuator whereby movement of the actuator drives the first material from the first container and the second material from the second container to the uterine cavity.

40. The instrument of claim 28 including: first drive means operable on movement thereof to supply fluid under pressure to said chamber surrounded by the sleeve means, first releasable means drivably connecting the first drive means with the actuator, a container for storing material, means for carrying the material from the container to the uterine cavity, plunger means cooperating with the container to force the material from the container into the uterine cavity, and second releasable means drivably connecting the plunger means with the actuator.

41. The instrument of claim 28 wherein: the dispensing means has a housing having a first recess to accommodate a part of the first releasable means to release the drive connection between the first drive assembly and the actuator and a second recess to accommodate a part of the second movable means to release the drive connection between the second movable means and the actuator after the drive connection between the first movable means and the actuator has been released.

42. An instrument for performing female sterilization comprising: means for containing fluid means for sealing the canals of the Fallopian tubes, dispensing means operable to move the fluid means from the means for containing the fluid means into the canals of the Fallopian tubes, said dispensing means including an expandable means positionable in the uterine cavity of the female and means operable to expand rapidly the expandable means to rapidly move the fluid means from the uterine cavity into the canals of the Fallopian tubes thereby sterilizing the female.

43. The instrument of claim 42 wherein: the expandable means is an expandable tubular sheet member.

44. An instrument for use in placing material in both canals of the Fallopian tubes of a female comprising: means for containing material for the canals of the Fallopian tubes, dispensing means having expandable means positionable in the uterine cavity of the female and means operable to move the material from the means for containing material to the uterine cavity, means for rapidly expanding the expandable means to substantially completely fill the uterine cavity to force the material from the uterine cavity into the canals of the Fallopian tubes, and control means connected to the means operable to move the material and the means for expanding, for automatically moving the material into the uterine cavity before the expandable means substantially completely fills the uterine cavity.

45. The instrument of claim 44 wherein: the expandable means comprises a balloon of material sufficiently flexible to generally conform to the shape of the uterine cavity of a female.

46. A dispensing apparatus comprising: housing means having a first chamber and a second chamber separated from the first chamber, first container means storing fluid located in the first chamber, second container means storing fluid located in the second chamber, means having a first passage connected to the first chamber and a second passage connected to the second chamber, means for fluidly coupling the first container means with the first passage and the second container means with the second passage, and means operable to first dispense fluid from the first container means into the first passage and to subsequently dispense fluid from the second container means into the second passage, said means for fluidly coupling including needle means for piercing at least one of said container means in response to operation of the means operable to dispense fluid from the chamber.

47. The apparatus of claim 46 wherein: said means for fluidly coupling includes needle means for piercing the first and second container means in response to operation of the means operable to dispense fluid from the chamber.

48. The apparatus of claim 46 wherein: the means operable to first dispense fluid from the first container means and to subsequently dispense fluid from the second container means includes an actuator and a first drive assembly operably coupled to the actuator and cooperating with the first container means to dispense fluid from the first container means in response to movement of the actuator.

49. The instrument of claim 48 including: lock means associated with the first drive assembly to stop movement of the drive assembly when a predetermined fluid pressure is present in the first passage.

50. The instrument of claim 48 wherein: the first drive assembly includes a first member, a second member movable relative to the first member, and biasing means holding the members in an extended position.

51. The instrument of claim 50 including: means acting on the biasing means to change the biasing force of the biasing means.

52. The instrument of claim 50 including: lock means cooperating with said members and dispensing means when the members are in a contracted position relative to each other to prevent movement of the drive assembly in the direction to increase fluid pressure to thereby limit the fluid pressure applied to the first passage.

53. The instrument of claim 48 wherein: the dispensing means includes a housing, said housing having a plurality of teeth facing the first drive assembly, said drive assembly having lock means engageable with one of the teeth to stop movement of the drive assembly when a predetermined fluid pressure is present in the first passage.

54. The instrument of claim 53 wherein: the lock means includes a body having a projection, and biasing means for moving the projection between adjacent teeth when the predetermined pressure is attained.

55. The apparatus of claim 48 including: releasable means to drivably connect the actuator with the first drive assembly.

56. The apparatus of claim 55 wherein: said releasable means includes a movable means mounted on the first drive assembly and engageable with the actuator to drivably connect the actuator to the first drive assembly.

57. A dispensing apparatus comprising: housing means having a first chamber and a second chamber, said second chamber separated from the first chamber, first container means storing first fluid located in the first chamber, second container means storing second fluid located in the second chamber, means having a first passage connected to the first chamber and a second passage connected to the second chamber, said second passage receiving second fluid from the second container means, means for fluidly coupling the first container means with the first passage, means for fluidly coupling the second container means with the second passage, said first container means comprising a cylinder having a chamber storing the first fluid, piston means movably positioned in the cylinder to confine the first fluid in the cylinder, means including a biasing member cooperating with the piston means to move the piston means into the cylinder whereby the first fluid is forced to flow into the first passage, and means operable to subsequently dispense the second fluid from the second container means into the second passage.

58. The dispensing apparatus of claim 57 including: means to bias the piston means out of the cylinder whereby the first fluid returns to the cylinder.

59. An instrument for placing fluid means in the canals of the Fallopian tubes of a female comprising: means for containing fluid means for use in the canals of the Fallopian tubes, dispensing means operable to move the fluid means from the means for containing the fluid means into the canals of the Fallopian tubes, said dispensing means including an expandable means positionable in the uterine cavity, means for moving the fluid means from the means for containing fluid means into the uterine cavity above the expandable means, further means operable to expand the expandable means to substantially fill the uterine cavity and thereby move the fluid means from the uterine cavity into the canals of the Fallopian tubes, said further means including control means for automatically controlling the pressure of the expandable means.

60. The instrument of claim 59 wherein: the expandable means is an expandable tubular sheet member.

61. The instrument of claim 60 wherein: said dispensing means includes an elongated tube, said expandable sheet member being mounted on the outer end of the tube, said further means and said control means being operable to supply fluid under controlled pressure to the chamber surrounded by the tubular sheet member and thereby expand the tubular sheet member to substantially fill the uterine cavity and move the fluid means from the uterine cavity into the canals of the Fallopian tubes.

62. An instrument for placing material into both canals of the Fallopian tubes open to the uterine cavity comprising: expandable means for displacing the uterine cavity, dispensing means connected to said expandable means operable to partly expand the expandable means, discharge material into the uterine cavity above the partly expanded expandable means, and fully expand the expandable means to force the material in the uterine cavity into the canals of the Fallopian tubes, said dispensing means including actuator means continuously movable to sequentially partly expand the expandable means, discharge material into the uterine cavity above the partly expanded expandable means and fully expand the expandable means to move the material from the uterine cavity into the canals of the Fallopian tubes.

63. The instrument of claim 62 wherein: the expandable means is an expandable tubular sheet material having low surface tension properties.

64. The instrument of claim 62 including: a tubular member connected to the dispensing means, means mounting the expandable means on the tubular member, head means having side material discharge openings on the forward end of the tubular member to direct material into the uterine cavity.

65. The instrument of claim 64 wherein: said head means includes an enlarged portion adapted to contact the fundus and space the discharge openings from the fundus.

66. The instrument of claim 62 wherein: the first means includes a first drive assembly operably coupled to the actuator means and movable in response to movement of the actuator means to supply fluid under pressure to a chamber surrounded by the expandable means whereby the expandable means expands to displace the uterine cavity.

67. The instrument of claim 66 including: lock means associated with the first drive assembly to stop the movement of the drive assembly when a predetermined fluid pressure is present in the chamber surrounded by the expandable means.

68. The instrument of claim 66 wherein: the dispensing means includes a housing, said housing having a plurality of teeth facing the first drive assembly, said drive assembly having lock means engageable with one of the teeth to stop movement of the drive assembly when a predetermined fluid pressure is present in the chamber surrounding the expandable means.

69. The instrument of claim 66 including: first releasable means to drivably connect the actuator means with the first drive assembly.

70. The instrument of claim 69 wherein: the first releasable means includes a movable means mounted in the first drive assembly and engageable with the actuator means to drivably connect the actuator means with the first drive assembly.

71. The instrument of claim 62 including: a container for storing the material, means for carrying the material from the container to the uterine cavity, and plunger means cooperating with the container and drivably connected to the actuator means whereby movement of the actuator means drives the material from the container to the uterine cavity.

72. The instrument of claim 71 including: second releasable means including a movable means mounted on said plunger means and engageable with said actuator means to drivably connect the actuator means to the plunger means.

73. The instrument of claim 62 including: a first container for storing a first material and a second container for storing a second material, means for carrying the first material and the second material and mixing said material from the first and second containers to the uterine cavity, and plunger means cooperating with the first container and second container and drivably connected to the actuator means whereby movement of the actuator means drives the first material from the first container and the second material from the second container to the uterine cavity.

74. The instrument of claim 62 including: first drive means operable on movement thereof to supply fluid under pressure to said chamber surrounded by the expandable means, first releasable means drivably connecting the first drive means with the actuator means, a container for storing material, means for carrying the material from the container to the uterine cavity, plunger means cooperating with the container to force the material from the container into the uterine cavity, and second releasable means drivably connecting the plunger means with the actuator means.

75. The instrument of claim 62 wherein: the dispensing means has a housing having a first recess to accommodate a part of the first releasable means to release the drive connection between the first drive assembly and the actuator means and a second recess to accommodate a part of the second movable means to release the drive connection between the second movable means and the actuator means after the drive connection between the first movable means and the actuator means has been released.

* * * * *

PO-1050
(5/69)

UNITED STATES PATENT OFFICE
CERTIFICATE OF CORRECTION

Patent No. 3,948,259                      Dated      April 6, 1976

Inventor(s)  Leé R. Bolduc and Eugene A. Dickhudt

It is certified that error appears in the above-identified patent and that said Letters Patent are hereby corrected as shown below:

IN THE SPECIFICATION:

Col. 1, line 43, delete "zince", inserting therefor --zinc--.
Col. 7, line 12, delete "form", inserting therefor --from--.
Col. 7, line 22, delete "in", inserting therefor --an--.
Col. 8, line 36, delete "container 22" and insert therefor --plunger 22--.
Col. 12, line 23, delete "realtion" and insert therefor --relation--.
Col. 16, line 21, delete "member 411" and insert therefor --member 441--.
Col. 16, line 37, delete "miimum" inserting therefor --minimum--.
Col. 17, line 31, delete "form" inserting therefor --from--.
Col. 19, line 62, delete "athe" inserting therefor --the--.
Col. 21, line 4, delete "adheisves" inserting therefor --adhesives--.

IN THE CLAIMS:
Col. 24, line 2, delete "femal" inserting therefor --female--.
Col. 24, lines 12 and 13 should be deleted in their entirety, and the following substituted therefor --2. The instrument of claim 1 wherein: said dispensing means second portion includes an expandable means positionable in--.
Col. 28, line 12, delete "to expand rapidly" insertint therefor --to rapidly expand--.

Signed and Sealed this

Tenth Day of August 1976

[SEAL]

Attest:

RUTH C. MASON
Attesting Officer

C. MARSHALL DANN
Commissioner of Patents and Trademarks